US010322873B2

(12) United States Patent
Conrad

(10) Patent No.: US 10,322,873 B2
(45) Date of Patent: Jun. 18, 2019

(54) DUST AND ALLERGEN CONTROL FOR SURFACE CLEANING APPARATUS

(71) Applicant: Omachron Intellectual Property Inc., Hampton (CA)

(72) Inventor: Wayne Ernest Conrad, Hampton (CA)

(73) Assignee: Omachron Intellectual Property Inc., Hampton, Ontario (CA)

( * ) Notice: Subject to any disclaimer, the term of this patent is extended or adjusted under 35 U.S.C. 154(b) by 201 days.

(21) Appl. No.: 15/393,055

(22) Filed: Dec. 28, 2016

(65) Prior Publication Data

US 2018/0177357 A1   Jun. 28, 2018

(51) Int. Cl.
*A47L 9/10* (2006.01)
*B65F 1/14* (2006.01)
*A47L 7/00* (2006.01)
*B08B 15/00* (2006.01)
*B08B 17/00* (2006.01)
(Continued)

(52) U.S. Cl.
CPC .............. *B65F 1/14* (2013.01); *A47L 7/0047* (2013.01); *A47L 9/106* (2013.01); *A47L 9/1683* (2013.01); *B08B 15/007* (2013.01); *B08B 17/00* (2013.01); *A61L 11/00* (2013.01); *B65F 1/105* (2013.01); *B65F 1/1607* (2013.01); *B65F 2210/129* (2013.01)

(58) Field of Classification Search
CPC .......... A47L 5/38; A47L 7/0047; A47L 9/106; A47L 9/16; A61L 11/00; B08B 15/007; B08B 17/00; B65F 1/105; B65F 1/14; B65F 2210/129
See application file for complete search history.

(56) References Cited

U.S. PATENT DOCUMENTS 2,567,171 A  9/1951 Anderson
4,598,838 A  7/1986 Zakrajsek
(Continued)

FOREIGN PATENT DOCUMENTS

CA  2658014 A1  9/2010
CN  1336154 A  2/2002
(Continued)

OTHER PUBLICATIONS

English translation of CN202173358, as published on Mar. 28, 2012.
(Continued)

*Primary Examiner* — Robert J Scruggs
(74) *Attorney, Agent, or Firm* — Philip C. Mendes da Costa; Bereskin & Parr LLP/S.E.N.C.R.L., s.r.l.

(57) ABSTRACT

An apparatus comprising one or more of a surface treatment apparatus having an air treatment member and a refuse container wherein at least one of the surface treatment apparatus and the refuse container is provided with one or more of (a) a dust control member providing a dust control agent comprising one or more of a liquid mist, positive ions and negative ions to an area below a dirt emptying outlet of a dirt collection region of the surface treatment apparatus; and, (b) a treatment applicator providing a treatment agent comprising one or more of a deodorizing agent, a disinfecting agent and a sanitizing agent to an interior volume of the air treatment member and an interior volume of the refuse container.

21 Claims, 32 Drawing Sheets

(51) Int. Cl.
*A47L 9/16* (2006.01)
*A61L 11/00* (2006.01)
*B65F 1/10* (2006.01)
*B65F 1/16* (2006.01)

(56) References Cited

U.S. PATENT DOCUMENTS

| | | | |
|---|---|---|---|
| 5,013,343 | A | 5/1991 | Miyamoto |
| 5,606,769 | A | 3/1997 | Tomasiak et al. |
| 6,129,213 | A | 10/2000 | Edwards |
| 6,193,787 | B1 | 2/2001 | Dyson et al. |
| 6,332,551 | B1 | 12/2001 | Copeland |
| 6,406,505 | B1 | 6/2002 | Oh et al. |
| 6,625,845 | B2 | 9/2003 | Matsumoto et al. |
| 7,488,362 | B2 | 2/2009 | Jeong et al. |
| 7,647,672 | B2 | 1/2010 | Nam et al. |
| 7,752,706 | B2 | 7/2010 | Goodger |
| 7,887,612 | B2 * | 2/2011 | Conrad ............... A47L 5/28 15/352 |
| 7,962,996 | B1 | 6/2011 | Mondello |
| 8,100,999 | B2 | 1/2012 | Ashbee et al. |
| 8,225,456 | B2 | 7/2012 | Hakan et al. |
| 8,388,900 | B2 * | 3/2013 | Benedek ............ A61L 9/015 422/1 |
| 8,444,731 | B2 | 5/2013 | Gomiciaga-Pereda et al. |
| 8,713,752 | B2 | 5/2014 | Kang |
| 8,732,892 | B2 | 5/2014 | Laliberte et al. |
| 8,978,197 | B2 | 3/2015 | Kang |
| 9,039,820 | B2 | 5/2015 | Han |
| 9,072,418 | B2 | 7/2015 | Hwang et al. |
| 9,155,434 | B2 | 10/2015 | Cho |
| 9,226,630 | B2 | 1/2016 | Chong et al. |
| 9,237,833 | B2 | 1/2016 | Hyun et al. |
| 9,271,618 | B2 | 3/2016 | Mantyla et al. |
| 9,315,308 | B2 | 4/2016 | Audet et al. |
| 9,924,846 | B2 | 3/2018 | Morin et al. |
| 2002/0078524 | A1 | 7/2002 | Schroter |
| 2004/0112022 | A1 | 6/2004 | Vuijk |
| 2005/0015916 | A1 | 1/2005 | Orubor |
| 2005/0132530 | A1 | 6/2005 | Macleod et al. |
| 2006/0137304 | A1 | 6/2006 | Jeong et al. |
| 2006/0156508 | A1 | 7/2006 | Khalil |
| 2006/0191099 | A1 | 8/2006 | Fry et al. |
| 2006/0278087 | A1 * | 12/2006 | Sepke ............... A47L 7/04 96/223 |
| 2007/0271724 | A1 | 11/2007 | Hakan et al. |
| 2008/0040883 | A1 | 2/2008 | Beskow et al. |
| 2008/0189898 | A1 | 8/2008 | Hughes |
| 2008/0256744 | A1 | 10/2008 | Rowntreer et al. |
| 2010/0229322 | A1 | 9/2010 | Conrad |
| 2010/0301147 | A1 * | 12/2010 | Harkess ............ A61L 11/00 241/23 |
| 2011/0119860 | A1 | 5/2011 | Marcil et al. |
| 2011/0219570 | A1 | 9/2011 | Conrad |
| 2012/0011679 | A1 | 1/2012 | Chong et al. |
| 2012/0030895 | A1 * | 2/2012 | Chong ............... A47L 9/108 15/323 |
| 2015/0020348 | A1 | 1/2015 | Miefalk et al. |
| 2015/0107047 | A1 | 4/2015 | Hyun et al. |
| 2016/0278591 | A1 | 9/2016 | Hutchins |
| 2016/0367094 | A1 | 12/2016 | Conrad |

FOREIGN PATENT DOCUMENTS

| | | |
|---|---|---|
| CN | 101015436 A | 8/2007 |
| CN | 101095604 A | 1/2008 |
| CN | 101288572 A | 10/2008 |
| CN | 101489453 A | 7/2009 |
| CN | 101489455 A | 7/2009 |
| CN | 101489457 A | 7/2009 |
| CN | 101489461 A | 7/2009 |
| CN | 101657133 A | 2/2010 |
| CN | 102188208 A | 9/2011 |
| CN | 102256523 A | 11/2011 |
| CN | 202173358 U | 3/2012 |
| DE | 3825773 A1 | 2/1990 |
| DE | 60201666 T2 | 6/2006 |
| DE | 60211663 T2 | 5/2007 |
| DE | 112006003479 T5 | 12/2008 |
| DE | 112007001314 T5 | 4/2009 |
| DE | 112007003039 T5 | 10/2009 |
| DE | 112007003052 T5 | 1/2010 |
| DE | 112010001135 T5 | 8/2012 |
| DE | 102012110765 A1 | 5/2014 |
| DE | 102014113797 A1 | 3/2016 |
| EP | 322387 A2 | 6/1989 |
| EP | 2628430 A2 | 8/2013 |
| EP | 2798992 A1 | 11/2014 |
| EP | 2848176 A1 | 3/2015 |
| EP | 2959817 A1 | 12/2015 |
| GB | 594471 A | 11/1947 |
| JP | 2009261501 A | 11/2009 |
| JP | 2010081968 A | 4/2010 |
| JP | 2014180647 A | 9/2014 |
| KR | 10-20050091821 A | 9/2005 |
| KR | 10-20050091824 A | 9/2005 |
| KR | 10-20050091826 A | 9/2005 |
| KR | 10-20050091829 A | 9/2005 |
| KR | 10-20050091830 A | 9/2005 |
| KR | 10-20050091833 A | 9/2005 |
| KR | 10-20050091834 A | 9/2005 |
| KR | 10-20050091835 A | 9/2005 |
| KR | 10-20050091836 A | 9/2005 |
| KR | 10-20050091837 A | 9/2005 |
| KR | 10-20050091838 A | 9/2005 |
| KR | 10-20060008365 A | 1/2006 |
| WO | 0243551 A1 | 6/2002 |
| WO | 2005053495 A1 | 6/2005 |
| WO | 2008135708 A1 | 11/2008 |
| WO | 2010102396 A1 | 9/2010 |
| WO | 201200967 A1 | 1/2012 |
| WO | 2012116956 A1 | 9/2012 |
| WO | 2016040601 A1 | 3/2016 |
| WO | 2016141960 A1 | 9/2016 |

OTHER PUBLICATIONS

English translation of CN102256523, as published on Nov. 23, 2011.
English translation of CN102188208, as published on Sep. 21, 2011.
English translation of CN101657133, as published on Feb. 24, 2010.
English translation of CN 101489461, as published on Jul. 22, 2009.
English translation of CN101489457, as published on Jul. 22, 2009.
English translation of CN101489455, as published on Jul. 22, 2017.
English translation of CN101489453, as published on Jul. 22, 2009.
English translation of CN101288572, as published on Oct. 22, 2008.
English translation of CN101095604, as published on Jan. 2, 2008.
English translation of CN101015436, as published on Aug. 15, 2007.
English translation of CN1336154, as published on Feb. 20, 2002.
English translation of DE112010001135, as published on Aug. 2, 2012.
English translation of DE112007003052, as published on Jan. 14, 2010.
English translation of DE112007003039, as published on Oct. 29, 2009.
English translation of DE112007001314, as published on Apr. 23, 2009.
English translation of DE112006003479, as published on Dec. 18, 2008.
English translation of DE102012110765, as published on May 15, 2014.
English translation of DE60211663, as published on May 10, 2007.
English translation of DE60201666, as published on Jun. 1, 2006.
English translation of JP2010081968, as published on Apr. 15, 2010.
English translation of JP2009261501, as published on Nov. 12, 2009.

(56) References Cited

OTHER PUBLICATIONS

English translation of KR20050091821, as published on Sep. 15, 2005.
English translation of KR20050091824, as published on Sep. 15, 2005.
English translation of KR20050091826, as published on Sep. 15, 2005.
English translation of KR20050091829, as published on Sep. 15, 2005.
English translation of KR20050091830, as published on Sep. 15, 2005.
English translation of KR20050091833, as published on Sep. 15, 2005.
English translation of KR20050091834, as published on Sep. 15, 2005.
English translation of KR20050091835, as published on Sep. 15, 2005.
English translation of KR20050091836, as published on Sep. 15, 2005.
English translation of KR20050091837, as published on Sep. 15, 2005.
English translation of KR20050091838, as published on Sep. 15, 2005.
English translation of KR 20060008365. as published on Jan. 26, 2006.
International Search Report and Written Opinion dated Feb. 13, 2018.
English machine translation of the Abstract of JP2014180647, published on Sep. 29, 2014.

\* cited by examiner

DUST AND ALLERGEN CONTROL FOR SURFACE CLEANING APPARATUS

FIELD

This disclosure relates generally to dust and allergen control for surface cleaning apparatus, and more specifically to systems and methods for constraining dust and other allergens during transfer of material collected by a surface cleaning apparatus to a garbage can or other waste receptacle.

INTRODUCTION

Various types of surface cleaning apparatus are known, including upright surface cleaning apparatus, canister surface cleaning apparatus, stick surface cleaning apparatus, hand surface cleaning apparatus and central vacuum systems.

Surface cleaning apparatus that use one or more cleaning stages (e.g. cyclonic cleaning stages) to remove particulate matter (e.g. dust and dirt) from an airstream are known. Frequently, a second cleaning stage, which may e.g. comprise a plurality of cyclones in parallel, is provided downstream of a first cleaning stage to remove particulate matter from the airstream exiting the first cleaning stage, e.g. by promoting the dis-entrainment of smaller particles from the airflow.

Particulate matter separated from an airstream by a cyclonic cleaning stage is frequently collected in one or more dirt collection chambers. Often, these collection chambers are removable from the surface cleaning apparatus, either on their own or as part of a removable cyclone assembly. Providing a detachable dirt collection chamber and/or cyclone assembly may allow a user to carry the collection chamber and its contents—e.g. to a refuse container, which may also be referred to as a garbage can, for emptying—without needing to carry or move the rest of the surface cleaning apparatus.

Typically, a dirt collection chamber is openable for accessing the interior of the dirt collection chamber, e.g. for emptying or cleaning. For example, the collection chamber may have one or more openable portions that are moveably connected to (e.g., pivotally) or removable from the collection chamber. Alternatively, or additionally, a cyclone assembly in which the collection chamber is provided may have one or more openable portions that e.g. provide access to an interior of a cyclone chamber.

Surface cleaning apparatus that collect particulate matter in an openable dirt collection chamber—which may be characterized as bagless' vacuum cleaners—may have one or more advantages as compared to surface cleaning apparatus in which particulate matter is collected in a bag or other non-openable collection vessel. For example, the effective suction provided at e.g. a dirty air inlet of the surface cleaning apparatus may be relatively constant, regardless of the amount of particulate matter in the dirt collection chamber.

However, dirt collected in an openable dirt collection chamber has to be transferred to a garbage can or the like to empty the openable dirt collection chamber.

SUMMARY

The following introduction is provided to introduce the reader to the more detailed discussion to follow. The introduction is not intended to limit or define any claimed or as yet unclaimed invention. One or more inventions may reside in any combination or sub-combination of the elements or process steps disclosed in any part of this document including its claims and figures.

In accordance with a first aspect of this disclosure, a lid for a refuse container may have an openable port that allows access to the interior of the refuse container without removing the lid from the refuse container. By positioning a dirt collection region of a surface cleaning apparatus in the port, the contents of the dirt collection region may be emptied into the refuse container without removing the lid. In such an arrangement, the lid may inhibit or prevent dust, allergens, or other particulate matter from escaping the interior of the refuse container while the particulate matter is being transferred from the dirt collection region to the refuse container.

For example, a surface cleaning apparatus may have a dirt collection region or chamber that is removable from the surface cleaning apparatus, either by itself or as part of a removable air treatment assembly, such as a removable cyclone assembly. A user may detach and carry such a dirt collection region to a refuse container for emptying or may carry the entire surface cleaning apparatus, such as a hand surface cleaning apparatus to the refuse container. If the dirt collection region is then opened above or in an open refuse container (e.g. a refuse container whose lid has been removed), then the contents will fall out due to gravity. However, lighter particulate matter may be entrained in air flow currents and may form a fine dust plume and/or may be carried to the floor adjacent the refuse container. In accordance with this aspect, a user may position the dirt collection region in an opened port of a lid of the refuse wherein the port is configured to inhibit or prevent dust, allergens, or other particulate matter from escaping the interior of the refuse container. For example, the port may be sized to be slightly larger than the dirt collection region, thereby providing a smaller annular gap between the lid and the dirt collection region, thereby reducing the likelihood that dust, allergens, or other particulate matter will escape from the interior of the refuse container. Alternatively, or in addition, the port may be provided with a gasket, or may be configured to close around the dirt collection container to inhibit or prevent dust, allergens, or other particulate matter from escaping the interior of the refuse container.

In accordance with this broad aspect, there is provided a lid for a refuse container, the lid moveable between a closed position in which the lid overlies an open upper end of the refuse container and an open position in which the refuse container may be emptied, the lid having an openable port operable between a closed position in which the lid closes the upper end of the refuse container and an open position in which a dirt collection region of an air treatment member of a surface cleaning apparatus is positioned in the port.

In some embodiments, in the open position, the lid may close around the dirt collection region.

In some embodiments, in the open position, the port may be sized to close around the dirt collection region whereby the refuse container is at least substantially sealed.

In some embodiments, the lid may comprise at least one moveable member which closes the port when the port is in the closed position and which is positioned adjacent a portion of the surface cleaning apparatus when the port is in the open position and the portion of the surface cleaning apparatus is positioned in the port with the dirt collection region overlying a bottom of the refuse container.

In some embodiments, the lid may comprise at least one moveable member which closes the port when the port is in the closed position and which abuts a portion of the surface cleaning apparatus when the port is in the open position and the portion of the surface cleaning apparatus is positioned in the port with the dirt collection region overlying a bottom of the refuse container.

In some embodiments, the lid may comprise at least one moveable member which closes the port when the port is in the closed position and which deflects inwardly into the refuse container when the port is in the open position.

In some embodiments, the at least one moveable member may be biased to the closed position.

In some embodiments, the at least one moveable member may comprise a plurality of sections each of which has an outer end that is located at a perimeter of the openable port and an inner end wherein, in the closed position, the sections close the port and, in the open position, at least a portion of the sections extend into the refuse container.

In some embodiments, the sections may be integrally formed as part of the lid.

In some embodiments, the lid may be formed of a resilient material.

In some embodiments, the dirt collection region may have an openable door and a door actuator and the lid may further comprise a lid actuator that is drivingly connected to the door actuator when the dirt collection region is positioned in the port.

In some embodiments the lid may further comprise a suction motor having a suction motor inlet end and a suction motor outlet end wherein, when the lid is in the closed position, the suction motor inlet end is in air flow communication with an interior volume of the refuse container and the suction motor outlet end is in air flow communication with the ambient atmosphere exterior to the refuse container.

Also in accordance with this broad aspect, there is also provided a garbage can comprising a container defining an interior volume and a lid moveable between a closed position in which the lid overlies an open upper end of the container and an open position in which the container may be emptied, the lid having an openable port operable between a closed position in which the lid closes the upper end of the container and an open position in which a dirt collection region of a surface cleaning apparatus is positioned in the port.

In some embodiments, in the open position, the lid may close around the dirt collection region.

In some embodiments, in the open position, the port may be sized to close around the dirt collection region whereby the container is at least substantially sealed.

In some embodiments, the lid may comprise at least one moveable member which closes the port when the port is in the closed position and which is positioned adjacent a portion of the surface cleaning apparatus when the port is in the open position and the portion of the surface cleaning apparatus is positioned in the port with the dirt collection region overlying a bottom of the refuse container.

In some embodiments, the lid may comprise at least one moveable member which closes the port when the port is in the closed position and which abuts a portion of the surface cleaning apparatus when the port is in the open position and the portion of the surface cleaning apparatus is positioned in the port with the dirt collection region overlying a bottom of the refuse container.

In some embodiments, the lid may comprise at least one moveable member which closes the port when the port is in the closed position and which deflects inwardly into the container when the port is in the open position.

In some embodiments, the at least one moveable member may be biased to the closed position.

In some embodiments, the at least one moveable member may comprise a plurality of sections each of which has an outer end that is located at a perimeter of the openable port and an inner end wherein, in the closed position, the sections close the port and, in the open position, at least a portion of the sections extends into the container.

In some embodiments, the sections may be integrally formed as part of the lid.

In some embodiments, the lid may be formed of a resilient material.

In some embodiments, the dirt collection region may have an openable door and a door actuator and the lid may further comprise a lid actuator that is drivingly connected to the door actuator when the dirt collection region is positioned in the port.

In some embodiments, the garbage can may further comprise a suction motor having a suction motor inlet end in air flow communication with the interior volume of the container and a suction motor outlet end is in air flow communication with the ambient atmosphere exterior to the container.

In accordance with a second aspect of this disclosure, a refuse container may be provided with a suction source to draw air from the interior volume of the container, which may reduce the air pressure within the refuse container. By drawing air from the interior volume of the container some, a substantial amount of, or substantially all of the dust, allergens, or other fine particulate matter dispersed into the air in the interior volume of the container, e.g., while particulate matter is being transferred from a dirt collection region of a surface cleaning apparatus through an opening of a refuse container (e.g., an open top of the refuse container), may be drawn from the interior volume towards the suction source or may be inhibited or prevented from escaping the interior of the refuse container through the opening and thereby remain in the interior volume to settle into the refuse container. Also, fine particulate matter which may be dispersed into the air above the interior volume of the refuse container upon emptying the dirt collection region may be drawn into the interior of the refuse container and may be drawn towards the suction source.

For example, a surface cleaning apparatus may have a dirt collection region or chamber that is removable from the surface cleaning apparatus, either by itself or as part of a removable air treatment assembly, such as a removable cyclone assembly. A user may detach and carry such a dirt collection region to a refuse container for emptying, and open the dirt collection region above or in an open refuse container (e.g. a refuse container whose lid has been removed), whereby gravity transfers at least some of the contents of the dirt collection region to the interior of the refuse container. However, opening the dirt collection region for emptying may result in a cloud or plume of fine dust or other particles billowing outwards from the opening of the dirt collection region and/or from the container into which the dirt collection region is being emptied. The particles in such a plume or cloud may be dispersed during the emptying process, resulting in a less than complete transfer from the dirt collection region to the interior of the refuse container. This may be considered undesirable by a user, particularly if the plume or cloud contains dust or other allergens to which the user is sensitive.

By providing a suction source to draw air from the interior volume of the refuse container, some or all of a plume of fine dust or other particles generated during the emptying of a dirt collection region of a surface cleaning apparatus may be drawn into the interior of the refuse container, which may result in a more controlled transfer of the contents of the dirt collection region to the refuse container.

In accordance with this second aspect, there is provided a garbage can comprising a container defining an interior volume and a lid moveable between a closed position and an open position and a suction motor having a suction motor inlet end in air flow communication with the interior volume of the container and a suction motor outlet end in air flow communication with the ambient atmosphere exterior to the container.

In some embodiments, the suction source may be provided on the lid.

In some embodiments, the suction source may be removably mounted to the lid.

In some embodiments, the suction source may be attached to the container.

In some embodiments, the suction source may be removably mounted to the container.

In some embodiments, the garbage can may further comprise an air flow path extending from the interior volume to a clean air outlet, the air flow path including the suction motor and an air treatment member.

In some embodiments, the air treatment member may comprise a cyclone.

In some embodiments, the garbage may further comprise a pre-motor filter positioned in the air flow path upstream of the suction motor.

In some embodiments, the garbage may further comprise a dust control member providing a dust control agent comprising one or more of a liquid mist, positive ions, and negative ions to the interior volume.

In some embodiments, the dust control agent may be provided when dirt is introduced to the interior volume.

In some embodiments, the dust control agent maybe automatically provided when dirt is introduced to the interior volume.

In accordance with this second aspect of this disclosure, a lid for a refuse container may be provided with a suction source to draw in air from an area proximate the opening of the container. By drawing air from the region near the opening of the container, dust, allergens, or other fine particulate matter dispersed in the air above or in the interior volume of the container—e.g. while particulate matter is being transferred from a dirt collection region of a surface cleaning apparatus to the refuse container—may be drawn into the interior of the refuse container, or inhibited or prevented from escaping the interior of the refuse container.

In accordance with this second broad aspect, there is provided a lid for a refuse container, the lid moveable between a closed position in which the lid overlies an open upper end of the refuse container and an open position in which the refuse container may be emptied wherein, when the lid is in the closed position, the suction motor inlet end is in air flow communication with an interior volume of the refuse container and the suction motor outlet end is in air flow communication with the ambient atmosphere exterior to the refuse container.

In some embodiments, the suction source may be removably mounted to the lid.

In some embodiments, the lid may further comprise an air flow path extending from the interior volume to a clean air outlet, the air flow path including the suction motor and an air treatment member.

In some embodiments, the air treatment member may comprise a cyclone.

In some embodiments, the lid may further comprise a pre-motor filter positioned in the air flow path upstream of the suction motor.

In some embodiments, the lid may further comprise a dust control member providing a dust control agent comprising one or more of a liquid mist, positive ions and negative ions to the interior volume.

In some embodiments, the dust control agent may be provided when dirt is introduced to the interior volume.

In some embodiments, the dust control agent may be automatically provided when dirt is introduced to the interior volume In accordance with a third aspect of this disclosure, a cyclone assembly of a surface cleaning apparatus may have a flexible closure member for enclosing an upper end of a refuse container. By deploying the flexible closure member about the refuse container prior to opening a dirt collection region of the cyclone assembly, an enclosed volume may be provided between an openable door of the dirt collection region and the interior of the refuse container. In such an arrangement, the closure member may inhibit or prevent dust, allergens, or other particulate matter from escaping the interior of the refuse container while this particulate matter is being transferred from the dirt collection region to the refuse container.

For example, a surface cleaning apparatus may have a cyclone assembly that is removable from the surface cleaning apparatus as a unit, and such a cyclone assembly may include a dirt collection region or chamber. A user may detach and carry such a cyclone assembly to a refuse container for emptying. Instead of opening the dirt collection region in the open above a refuse container or in an open refuse container and relying on gravity to transfer the contents of the dirt collection region to the interior of the refuse container, the flexible closure member may be deployed about an upper end of the refuse container before opening the dirt collection region, which may result in a more controlled transfer of the contents of the dirt collection region to the refuse container. In particular, lighter collected matter which may be entrained in the air when the dirt collection region is opened may be contained within a closed or generally closed volume and may therefore be isolated or substantially isolated for air currents which may create a fine dust plume or, if such a plume forms, it will be within the interior of the hood and therefore the plume will be contained.

In accordance with this third aspect, there is provided a cyclone bin assembly for a surface cleaning apparatus, the cyclone bin assembly comprising: a dirt collection region for a cyclone, the dirt collection region having an openable door; and, a flexible closure member moveable to a deployed position wherein a first portion of the closure member is provided on the cyclone bin assembly and a second portion of the closure member closes the upper end of a refuse container, whereby when the closure member is in the deployed position, a closed volume is provided which includes an interior volume of the refuse container and the openable door is located in the closed volume.

In some embodiments, the flexible closure member may be mounted to an exterior surface of the cyclone bin assembly.

In some embodiments, the flexible closure member may be air impermeable.

In some embodiments, the closure member may be removably mountable to the cyclone bin assembly.

In some embodiments, the closure member may be moveable to a retracted position in which the second portion of the closure member is retracted and secured to the cyclone bin assembly.

In some embodiments, the second portion of the closure member may have a securing member which retains the second portion on the refuse container when the flexible closure member is in the deployed position.

In some embodiments, the securing member may comprise at least one of a resilient member and a drawstring.

In some embodiments, the flexible closure member may comprise a hood.

In some embodiments, the cyclone bin assembly may further comprise an actuator for the openable door and, when the flexible closure member is in the deployed position, the actuator is exterior to the closed volume.

In accordance with this third aspect, there is also provided a dirt collection system comprising: a cyclone bin assembly comprising: a dirt collection region for a cyclone, the dirt collection region having an openable door; and, a flexible closure member moveable to a deployed position wherein a first portion of the closure member is provided on the cyclone bin assembly and a second portion of the closure member closes the upper end of a refuse container, whereby when the closure member is in the deployed position, a closed volume is provided which includes an interior volume of the refuse container and the openable door is located in the closed volume; and, a refuse container comprising a suction motor having a suction motor inlet end in air flow communication with the interior volume of the refuse container and a suction motor outlet end in air flow communication with the ambient atmosphere exterior to the refuse container.

In accordance with this third aspect, there is also provided a dirt collection apparatus comprising: a dirt collection region having an openable door; and, a flexible closure member moveable to a deployed position wherein a first portion of the closure member is provided on the dirt collection apparatus and a second portion of the closure member closes the upper end of a refuse container, whereby when the closure member is in the closed position, a closed volume is provided which includes an interior volume of the refuse container and the openable door is located in the closed volume.

In some embodiments, the flexible closure member may be mounted to an exterior surface of the dirt collection apparatus.

In some embodiments, the flexible closure member may be air impermeable.

In some embodiments, the closure member may be removably mountable to the cyclone bin assembly.

In some embodiments, the closure member may be moveable to a retracted position in which the second portion of the closure member is retracted and secured to the dirt collection apparatus.

In some embodiments, the second portion of the closure member may have a securing member which retains the second portion on the refuse container when the flexible closure member is in the deployed position.

In some embodiments, the securing member may comprise at least one of a resilient member and a drawstring.

In some embodiments, the flexible closure member may comprise a hood.

In some embodiments, the dirt collection apparatus may further comprise an actuator for the openable door and, when the flexible closure member is in the deployed position, the actuator is exterior to the closed volume.

In accordance with this third aspect, there is also provided a dirt collection system comprising: a dirt collection apparatus comprising: a dirt collection region having an openable door; and, a flexible closure member moveable to a deployed position wherein a first portion of the closure member is provided on the dirt collection apparatus and a second portion of the closure member closes the upper end of a refuse container, whereby when the closure member is in the closed position, a closed volume is provided which includes an interior volume of the refuse container and the openable door is located in the closed volume; and, a refuse container comprising a suction motor having a suction motor inlet end in air flow communication with the interior volume of the refuse container and a suction motor outlet end in air flow communication with the ambient atmosphere exterior to the refuse container.

In accordance with a fourth aspect of this disclosure, a refuse container may be provided with a dust control system to provide a dust control agent towards the interior volume of the refuse container, and/or towards an area above the interior volume of the refuse container, e.g., below a dirt emptying outlet of a dirt collection region of a surface treatment apparatus. By providing a dust control agent into or above the interior volume of the container, the dispersal of dust, allergens, or other fine particulate matter into the air, e.g. while particulate matter is being transferred from a dirt collection region of a surface cleaning apparatus to the refuse container, may be inhibited or prevented. For example, by wetting the particulate matter, the particulate matter will be heavier and less likely to form a dust plume. Alternatively, the particulate matter may acquire a charge during the passage through a cyclone. By at least partially neutralizing any such a charge that the particulate matter may acquire, the particulate matter will be less likely to spread out and form a dust plume when the particulate matter exits a dirt collection region.

Alternatively, or additionally, the refuse container may be provided with a treatment applicator to provide a treatment agent (e.g. a deodorizing agent, a disinfecting agent, a sanitizing agent) to an interior volume of the refuse container. By providing such a treatment agent, one or more negative aspects of dust, allergens, or other particulate matter located in the interior volume of the container, e.g. unpleasant odor, possible bacterial or microbial growth, may be inhibited or eliminated.

Also in accordance with this fourth aspect, a surface treatment apparatus may be provided with a dust control system to provide a dust control agent towards an openable door of a dirt collection region of the surface cleaning apparatus, and/or towards an area proximate the openable door. By providing a dust control agent towards an openable door of a dirt collection region, the dispersal of dust, allergens, or other fine particulate matter into the air when the openable door is opened, e.g. while particulate matter is being transferred from the dirt collection region to a refuse container, may be inhibited or prevented.

Alternatively, or additionally, the surface treatment apparatus may be provided with a treatment applicator to provide a treatment agent (e.g. a deodorizing agent, a disinfecting agent, a sanitizing agent) to an interior volume of an air treatment member of the surface treatment apparatus (e.g. a dirt collection region). By providing such a treatment agent, one or more negative aspects of dust, allergens, or other particulate matter located in the interior volume of the air treatment member, e.g. unpleasant odor, possible bacterial or microbial growth, may be inhibited or eliminated.

In accordance with this fourth aspect, there is provided an apparatus comprising one or more of a surface treatment apparatus having an air treatment member and a refuse container wherein at least one of the surface treatment apparatus and the refuse container comprises one or more of: a) a dust control member providing a dust control agent comprising one or more of a liquid mist, positive ions, and negative ions to an area below a dirt emptying outlet of a dirt collection region of the surface treatment apparatus; and, b) a treatment applicator providing a treatment agent comprising one or more of a deodorizing agent, a disinfecting agent, and a sanitizing agent to an interior volume of the air treatment member and an interior volume of the refuse container.

In some embodiments, the one of the surface treatment apparatus and the refuse container may comprise both the dust control member and the treatment applicator.

In some embodiments, the dust control member may comprise one or more nozzles directed to the area below the dirt emptying outlet of the dirt collection region of the surface treatment apparatus.

In some embodiments, the nozzles may introduce the dust control agent to a location below the dirt emptying outlet and above the bottom of the refuse container.

In some embodiments, the apparatus may further comprise a hood which, when the dirt emptying outlet is open and the hood is in a deployed position, a closed volume is provided that includes the interior volume of the refuse container and an interior volume of the dirt collection region and the nozzles introduce the dust control agent into the closed volume.

In some embodiments, the surface cleaning apparatus may comprise a dirt separation member having the dirt emptying outlet and the nozzles are located around at least part of the perimeter of the dirt separation member.

In some embodiments, the nozzles may be provided on the refuse container.

In some embodiments, the dust control member may be automatically actuated when the dirt emptying outlet is opened.

In some embodiments, the dust control member may be automatically actuated prior to the dirt emptying outlet being opened.

In some embodiments, the one of the surface treatment apparatus and the refuse container which has the dust control member may further comprise a dust control agent reservoir.

In some embodiments, the refuse container may further comprise a suction motor having a suction motor inlet end in air flow communication with the interior volume of the refuse container and a suction motor outlet end in air flow communication with the ambient atmosphere exterior to the refuse container.

In some embodiments, the apparatus may further comprise an air flow path extending from the interior volume to a clean air outlet, the air flow path including the suction motor and a refuse container air treatment member.

In some embodiments, the refuse container air treatment member may comprise a cyclone.

In some embodiments, the apparatus may further comprise a pre-motor filter positioned in the air flow path upstream of the suction motor.

In some embodiments, the treatment agent may comprise one of more of ozone, UV light, and hydrogen peroxide.

In some embodiments, the treatment agent may comprise ozone and the refuse container further comprises an air flow path extending from the interior volume of the refuse container to a clean air outlet, the air flow path including the suction motor and an ozone destructor material.

In some embodiments, the apparatus may further comprises a hood which, when the dirt emptying outlet is open and the hood is in a deployed position, a closed volume is provided that includes the interior volume of the refuse container and an interior volume of the dirt collection region and the treatment agent is introduced into the closed volume.

In some embodiments, the treatment agent may be provided at pre-set intervals.

In some embodiments, the treatment agent may be provided after a pre-set number of uses of the surface cleaning apparatus.

In some embodiments, the treatment agent may be provided by manual activation.

In some embodiments, the treatment agent may be provided subsequent to emptying of the dirt collection region.

In accordance with a fifth aspect of this disclosure, a surface cleaning apparatus may be configured to selectively draw air from a dirt collection region of the surface cleaning apparatus, such that air pressure in the dirt collection region may be reduced below the pressure of the ambient atmosphere when an openable door of the dirt collection region is in an open position. By drawing air from the interior volume of the dirt collection region, the dispersal of dust, allergens, or other fine particulate matter into the air when the openable door is opened, e.g. while particulate matter is being transferred from the dirt collection region to a refuse container, may be inhibited or prevented. For example, air may be drawn directly from a dirt chamber and/or from a cyclone which is in air flow communication with a dirt chamber via a cyclone chamber dirt outlet. The air may be drawn towards a suction motor and may be filtered before and/or after passage by or through the suction motor. The suction motor may be the same suction motor as used to clean a surface and/or a separate suction motor.

For example, a surface cleaning apparatus may have a cyclone assembly that includes a dirt collection region or chamber having an openable door. A user may position such a cyclone assembly above a refuse container for emptying. Prior to or while or after opening the door of the dirt collection region, the air pressure in the dirt collection region may be reduced to below that of the ambient air, which may result in a net inflow of air into the dirt collection region, thereby drawing finer dust, allergens, or other fine particulate matter towards the dirt collection region and/or maintaining finer dust, allergens, or other fine particulate matter in the dirt collection region. Accordingly, emptying of the dirt collection region may result in no dust plume, or a reduced dust plume, being formed in the air which may fall outside a refuse container. For example, larger dirt particles collected in the dirt collection region may be directed by gravity to the interior of the refuse container, while some or all of the finer dust or other smaller particles that may have otherwise formed a cloud or plume billowing outwards from the opening of the dirt collection region may be drawn towards the opening of the dirt collection region.

In accordance with this fifth aspect, there is provided a surface cleaning apparatus comprising: a) an air flow path extending from a dirty air inlet to a clean air outlet and comprising a main air treatment member having a dirt collection region having an openable door; and, b) a main suction motor provided in the air flow path, wherein the dirt collection region is exposed to sub-atmospheric pressure when the openable door is in an open position.

In some embodiments, the dirt collection region may be automatically exposed to sub-atmospheric pressure when the openable door is opened.

In some embodiments, the dirt collection region may be automatically exposed to sub-atmospheric pressure prior to the openable door opening.

In some embodiments, the main suction motor may be utilized to provide the sub-atmospheric pressure to the dirt collection chamber.

In some embodiments, the main suction motor may be operable in a cleaning mode in which the main suction motor is used to draw air from the dirty air inlet, through the main air treatment member to the clean air outlet and an emptying mode in which the main suction motor is utilized to provide the sub-atmospheric pressure to the dirt collection chamber and the main suction motor is operated at a lower power level during the emptying mode.

In some embodiments, the main suction motor may produce sufficient suction to create an air flow of 0.1 Cubic Feet per Minute (CFM) to 1.5 CFM per square inch of opening area during the emptying mode, preferably 0.25 CFM to 1.25 CFM per square inch of opening during the emptying mode and more preferably 0.50 CFM to 1.00 CFM per square inch of opening area during the emptying mode.

In some embodiments, the main suction motor may be operable in a cleaning mode in which the main suction motor is used to draw air from the dirty air inlet, through the main air treatment member to the clean air outlet and an emptying mode in which the main suction motor is utilized to provide the sub-atmospheric pressure to the dirt collection chamber, wherein a first pre-motor filter is positioned in a main downstream portion of the air flow path from the main air treatment member to the main suction motor during the cleaning mode and an alternate air treatment member is provided in an alternate downstream air flow path from the main air treatment member to the main suction motor during the emptying mode.

In some embodiments, the surface cleaning apparatus may further comprise a main closure member associated with the main downstream portion of the air flow path and an alternate closure member associated with the alternate downstream air flow path, each of the main closure member and the alternate closure member moveable between an open position and a closed position wherein, during the cleaning mode, the main closure member is open and the alternate closure member is closed whereby the main suction motor is in air flow communication with the main air treatment member via the main downstream portion of the air flow path and in the emptying mode the main closure member is closed and the alternate closure member is open whereby the main suction motor is in air flow communication with the main air treatment member via the alternate downstream air flow path.

In some embodiments, the alternate air treatment member may comprise a filter.

In some embodiments, the surface cleaning apparatus may further comprise an emptying mode suction motor which provides the sub-atmospheric pressure to the dirt collection chamber.

In some embodiments, the emptying mode suction motor may produce a sub-atmospheric pressure less than a pressure in the main air treatment member during operation of the main suction motor.

In some embodiments, the main suction motor may produce sufficient suction to create an air flow of 0.1 CFM to 1.5 CFM per square inch of opening area during the emptying mode, preferably 0.25 CFM to 1.25 CFM per square inch of opening during the emptying mode and more preferably 0.50 CFM to 1.00 CFM per square inch of opening area during the emptying mode.

In some embodiments, a portion of the air flow path may connect the emptying mode suction motor in air flow communication with the dirt collection region during an emptying mode of the dirt collection region.

In some embodiments, the portion of the air flow path may be positioned upstream of the main air treatment member.

In some embodiments, an emptying mode air treatment member may be positioned in the portion of the air flow path.

In some embodiments, the surface cleaning apparatus may comprise a main closure member associated with the portion of the air flow path the main closure member being moveable between an open position and a closed position wherein, during the cleaning mode, the main closure member is closed whereby air travels from the dirty air inlet to the main air treatment member without contacting the emptying mode air treatment member and, in the emptying mode the main closure member is opened whereby air travels from the main air treatment member and through the emptying mode air treatment member.

In some embodiments, the emptying mode air treatment member may comprise a filter.

In some embodiments, the main air treatment member may comprise a cyclone.

In some embodiments, the dirt collection region may comprise a dirt collection chamber exterior to the cyclone.

It will be appreciated by a person skilled in the art that an apparatus or method disclosed herein may embody any one or more of the features contained herein and that the features may be used in any particular combination or sub-combination.

These and other aspects and features of various embodiments will be described in greater detail below.

BRIEF DESCRIPTION OF THE DRAWINGS

For a better understanding of the described embodiments and to show more clearly how they may be carried into effect, reference will now be made, by way of example, to the accompanying drawings in which.

Figure 1:
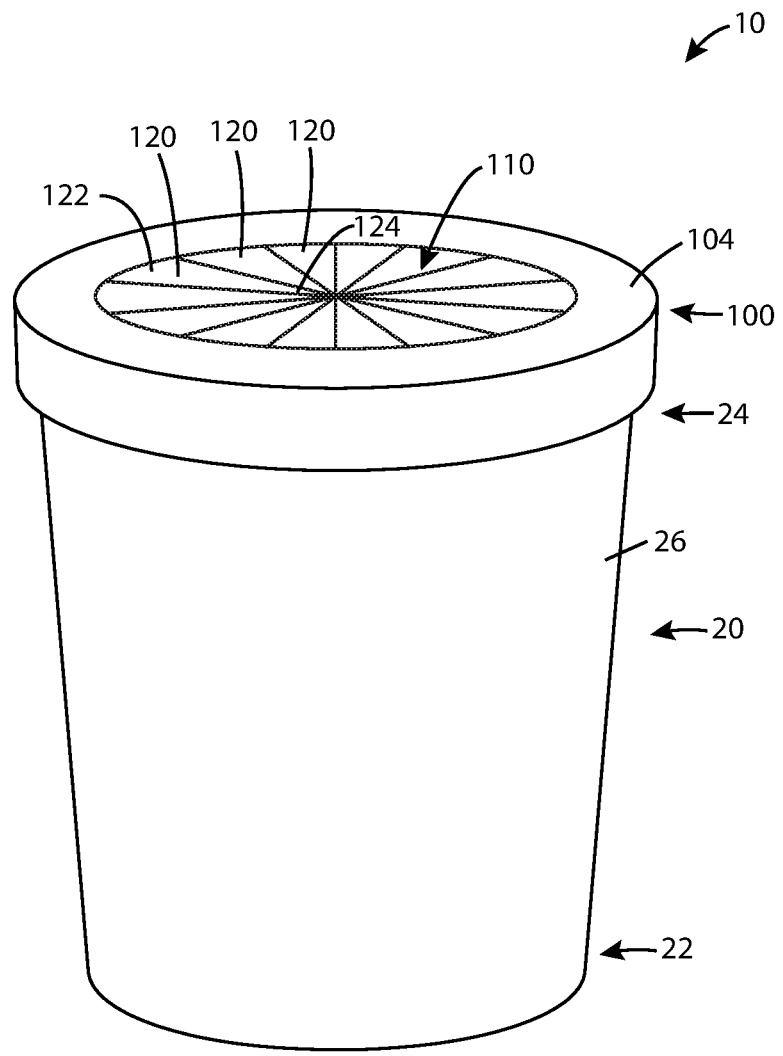
FIG. 1 is a perspective view of a container and a lid having an openable port in accordance with one embodiment.
Figure 2:
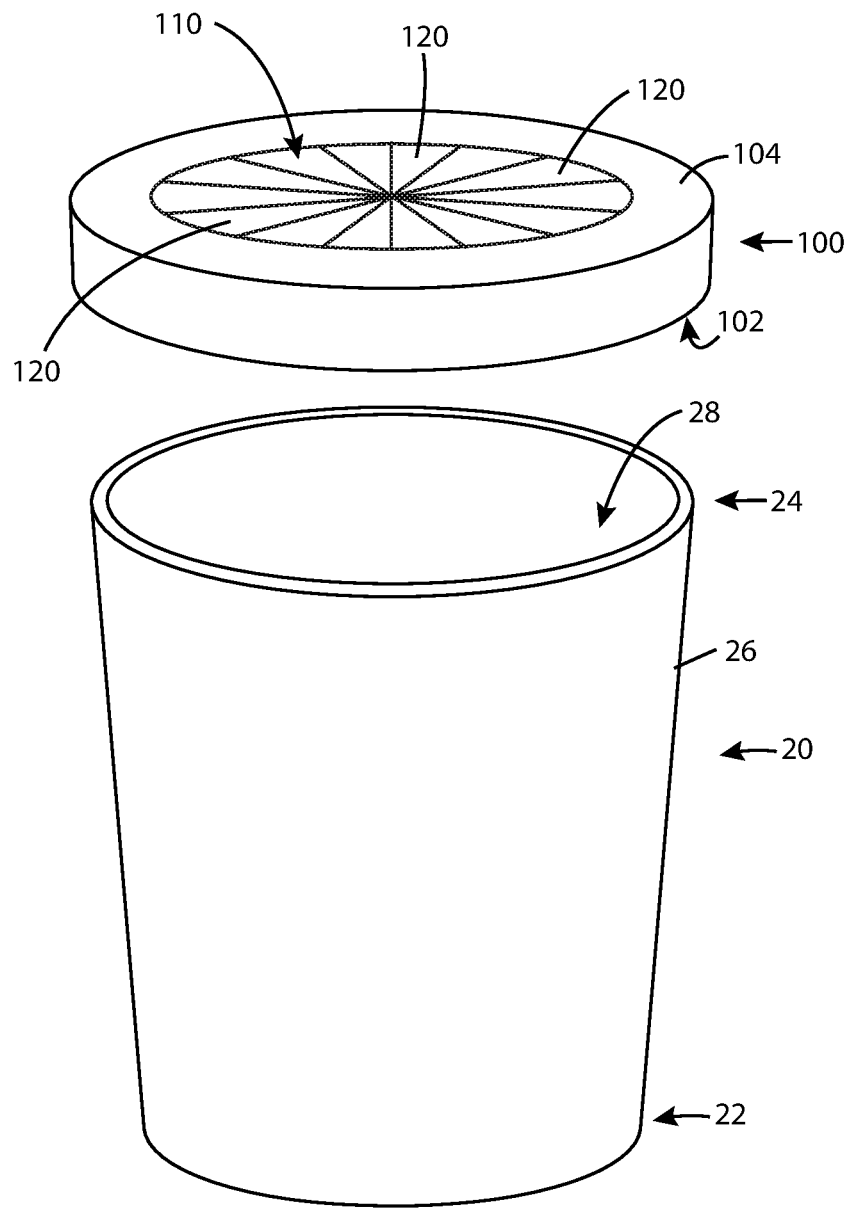
FIG. 2 is a perspective view of the container and lid of FIG. 1 with the lid in an open position and overlying the open interior of the container.
Figure 3:
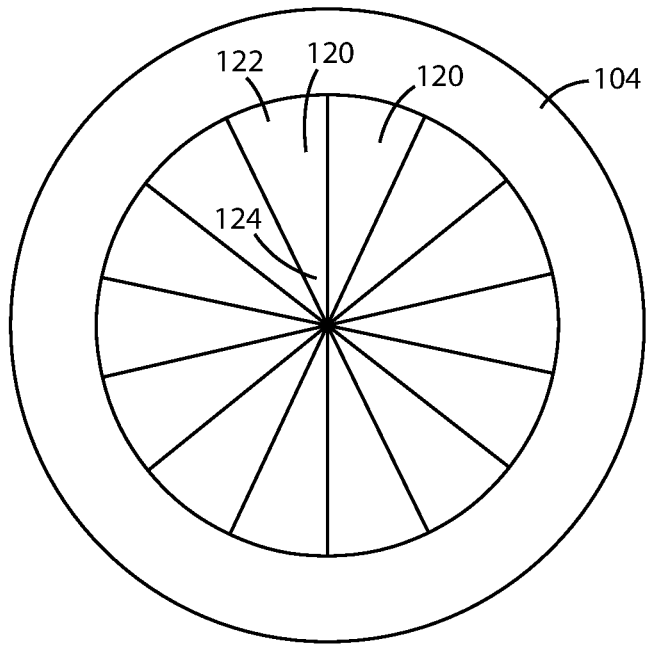
FIG. 3 is a top view of the lid of FIG. 1, with the openable port in a closed position.
Figure 4:
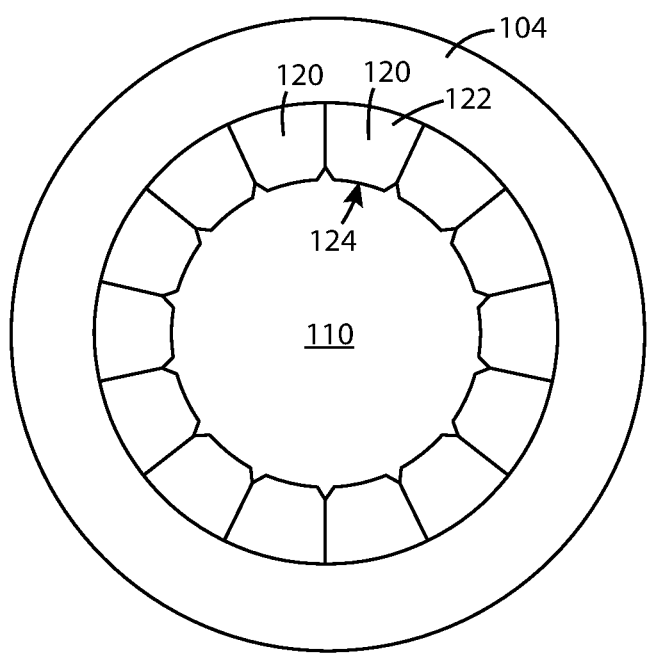
FIG. 4 is a top view of the lid of FIG. 1, with the openable port in an open position.

The drawings included herewith are for illustrating various examples of articles, methods, and apparatuses of the teaching of the present specification and are not intended to limit the scope of what is taught in any way.

DESCRIPTION OF EXAMPLE EMBODIMENTS

Various apparatuses, methods and compositions are described below to provide an example of an embodiment of each claimed invention. No embodiment described below limits any claimed invention and any claimed invention may cover apparatuses and methods that differ from those described below. The claimed inventions are not limited to apparatuses, methods and compositions having all of the features of any one apparatus, method or composition described below or to features common to multiple or all of the apparatuses, methods or compositions described below. It is possible that an apparatus, method or composition described below is not an embodiment of any claimed invention. Any invention disclosed in an apparatus, method or composition described below that is not claimed in this document may be the subject matter of another protective instrument, for example, a continuing patent application, and the applicant(s), inventor(s) and/or owner(s) do not intend to abandon, disclaim, or dedicate to the public any such invention by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures, and components have not been described in detail so as not to obscure the example embodiments described herein. Also, the description is not to be considered as limiting the scope of the example embodiments described herein.

The terms "an embodiment," "embodiment," "embodiments," "the embodiment," "the embodiments," "one or more embodiments," "some embodiments," and "one embodiment" mean "one or more (but not all) embodiments of the present invention(s)," unless expressly specified otherwise.

The terms "including," "comprising," and variations thereof mean "including but not limited to," unless expressly specified otherwise. A listing of items does not imply that any or all of the items are mutually exclusive, unless expressly specified otherwise. The terms "a," "an," and "the" mean "one or more," unless expressly specified otherwise.

In the examples discussed herein, the dirt collection region (or dirt collection chamber) from which dust, allergens, or other particulate matter may be transferred to a refuse container or other receptacle may be associated with any suitable type of surface cleaning apparatus, such as an upright vacuum cleaner, a canister type vacuum cleaner, a hand vacuum cleaner, a stick vacuum cleaner, a wet-dry type vacuum cleaner, a carpet extractor, and the like.

The flowing is a general description of a garbage can which may be used with any aspect of this disclosure.

Referring to FIGS. 1-8, a container 20 and a lid 100 are shown generally and collectively as 10. Container 20 may be referred to as a refuse container, and the container 20 and lid 100 may be referred to collectively as a garbage can. The container 20 includes an upper end 24 and a closed lower end 22, and a sidewall 26 extending between the lower and upper ends 22, 24. Sidewall 26 and lower end 22 define an interior volume 28 of the container 20. The lid 100 is configured to rest on or engage with the upper end 24 of container 20, such that the lid overlies all or substantially all of upper end 24. In such a closed configuration, lid 100 inhibits or prevents access to the interior volume 28 of container 20. Lid 100 is preferably removable from refuse container 20, to e.g. facilitate emptying of the container. It will be appreciated that container 20 and a lid 100 may be of any configuration known in the art and may be lockingly secured to each other by any means known in the art.

In the examples discussed herein, dust, allergens, or other particulate matter are described as being transferred into interior volume 28 of refuse container 20. It will be appreciated that a secondary container, such as a refuse or garbage bag (e.g. a plastic or paper container, which may be characterized as a disposable container) may be removably positioned in refuse container 20, e.g. lining all or substantially all of the interior volume 28. For example, an upper portion of a secondary container may be positioned between container 20 and lid 100, with a lower portion of the secondary container positioned adjacent or in abutment with lower end 22 of container 20. In such an arrangement, refuse deposited into the container 20 is actually deposited into the secondary container, and the secondary container maybe periodically removed from container 20 to transfer the collected refuse to e.g. a larger household refuse container, such as a container from which a municipality or other service provider may collect refuse for transport to a landfill, an incinerator, and the like.

As exemplified in FIGS. 1-8, lid 100 has an upper surface 104 and a lower surface 102. The lower surface 102 is configured to overlie upper end 24 of container 20, in order to substantially or entirely enclose interior volume 28 of container 20. For example, as exemplified in FIG. 5, lower surface 102 may have a channel 108 that is dimensioned to overlie and engage with the sidewall 26 at the upper end 24 of container 20. Alternatively, the lower surface 102 and/or the upper end 24 may be provided in another configuration for cooperative engagement, for example upper end 24 may have a channel in the top surface of sidewall 26 and lower surface 102 may have a one or more downwardly extending projections for engaging such a channel.

Figure 10:
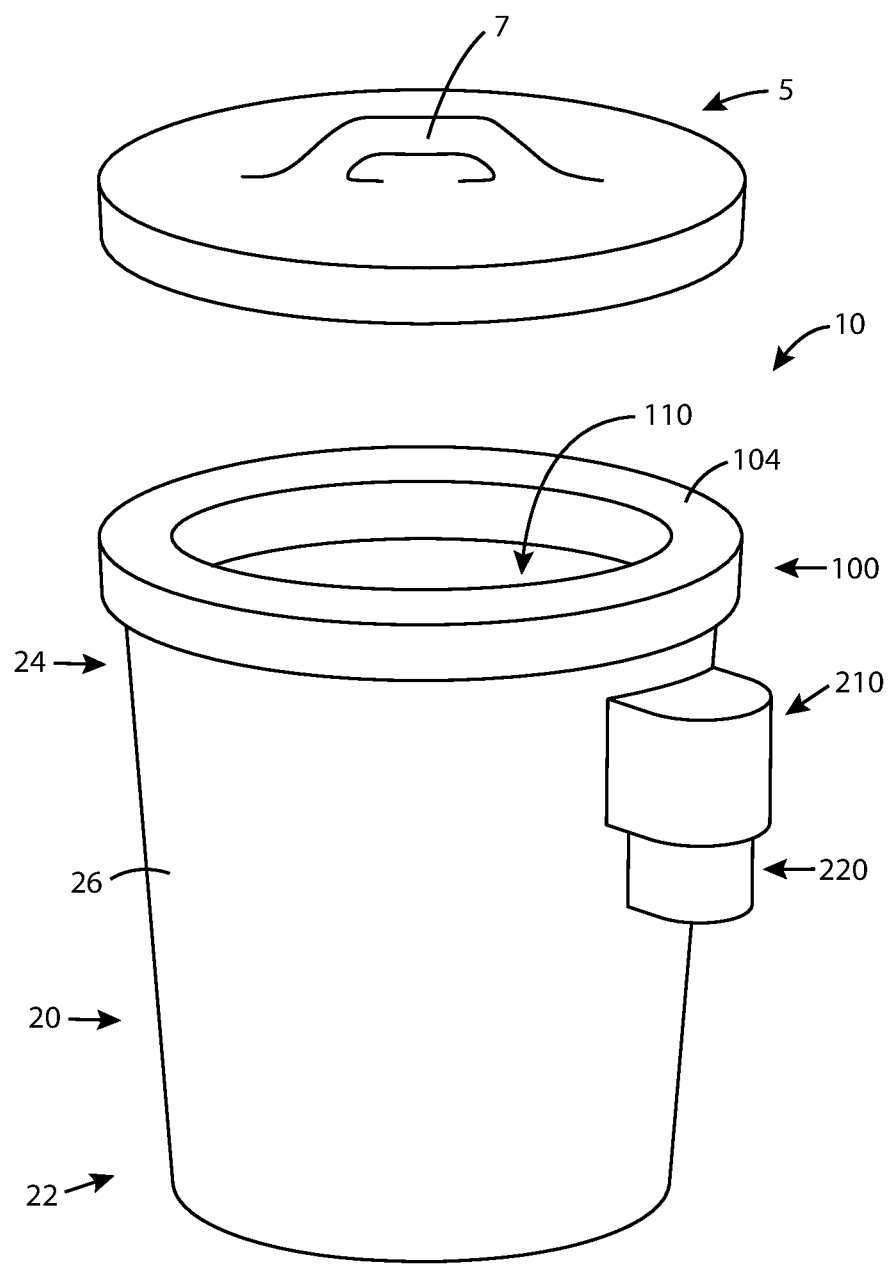
FIG. 10 is a perspective view of a container, a first lid having an open port, a second lid in a removed position, and a suction source in accordance with one embodiment.

In some of the embodiment disclosed herein, the lid may include an operating component and/or part of a fluid flow passage and/or an ion emitter. In such a case, a two part lid system may be used. In such a case, as exemplified in FIG. 10, the lid for the container 20 may comprise a first lid 100 and a second lid 5. In FIG. 10, a second or upper lid 5 is also shown in a removed position. Upper lid 5 is configured to rest on or engage with the upper surface 104 of lid 100, such that the second lid 5 overlies all or substantially all of port 110. Lid 5 is preferably removable from lid 100. In the illustrated embodiment, lid 5 has a handle 7, although such a handle may not be provided in alternative embodiments.

In some embodiments, second or upper lid 5 may also be configured to rest on or engage with the upper end 24 of container 20, such that the lid overlies all or substantially all of upper end 24. For example, second lid 5 and container 20 may have been purchased or otherwise acquired as a set, and first or inner lid 100 may be configured to act as a retrofit or to otherwise provide some or all of the dust control features and/or functionality as disclosed herein.

An advantage of using a second lid 5 is that an operating component and/or part of a fluid flow passage and/or an ion emitter need not be provided with container 20. Instead, they may be provided in or on or as part of the lid. When the container is to be emptied, first lid 100 may be removed and second lid 5 used to close container 20. Container 20 may then be taken to the end of a driveway to be emptied by a municipal garbage service without concern that an operating component and/or part of a fluid flow passage and/or an ion emitter may be damaged by workers when emptying container 20.

Refuse Container Lid Having an Openable Port

The following is a general description of a lid for a refuse container having an openable port and other features set out herein that may be used by itself or in combination with one or more embodiments disclosed herein, including one or more of a refuse container having a suction source, a cyclone bin assembly having a deployable closure member, dust control systems for refuse containers or surface treatment apparatus, and dust treatment systems for refuse containers or surface treatment apparatus. The following description contains various features of a lid for a refuse container having an openable port that may be used individually or in any combination or sub-combination.

In accordance with this aspect, lid 100 has an aperture or port 110 extending between upper surface 104 and lower surface 102. Port 110 is operable between a closed position in which particulate matter (e.g. dirt, dust, allergens, and the like) is inhibited or preferably prevented from passing through port 110, and an open position. Preferably, a closure member of port 110 is biased towards the closed position. It will be appreciated that port 110 may occupy part or all of lid 100 other than the portion of lid that seats on refuse container 20. It will be appreciated that In the illustrated example, a number of moveable members or flanges 120 are provided on the interior perimeter of port 110. Each moveable flange 120 extends inwardly from an outer end 122 towards an inner end 124 located at or proximate the center of port 110, and the members 120 are dimensioned such that when the members are each substantially parallel to lid 100, the aperture or port 110 is substantially or preferably completely closed by the flanges 120. Preferably, flanges 120 are flexible, and may be resiliently biased towards a closed position, e.g., a position in which the members are substantially parallel to the remainder of the horizontally extending portion of lid 100.

Alternatively, the moveable members or flanges may be of any other suitable configuration, including, for example a configuration in which the members open like an iris, a sliding panel or the like.

Moveable members or flanges 120 may be secured to lid 100 using any suitable method, such as using one or more mechanical fasteners, an adhesive, or the like. Alternatively, the lid 100 and flanges 120 may be integrally formed, e.g. via injection molding.

The operation of lid 100 in controlling dust, allergens, and other particulate matter when emptying a dirt collection region of a surface cleaning apparatus will now be discussed with reference to FIGS. 5-8.

Figure 5:
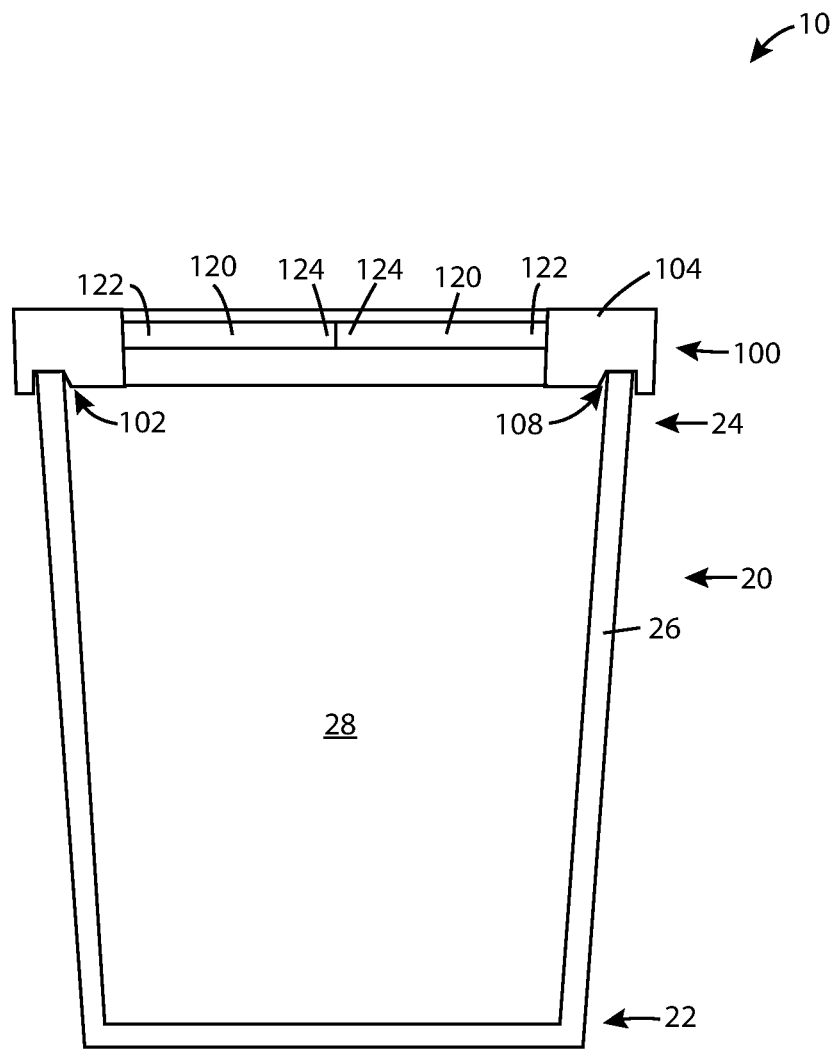
FIG. 5 is a cross section view of the container and lid of FIG. 1, taken along line 5-5, with the openable port in a closed position.

In FIG. 5, lid 100 is resting on and overlying upper end 24 of container 20. Flanges 120 are substantially parallel to lid 100, cooperatively closing port 110 in lid 100.

Figure 6:
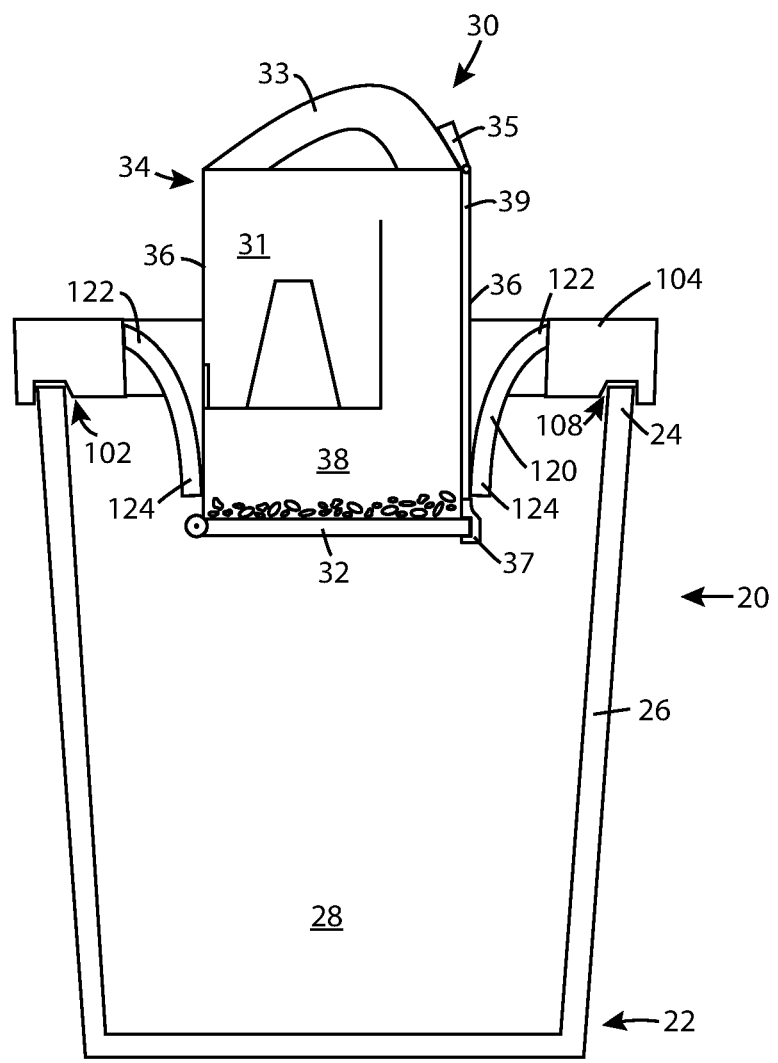
FIG. 6 is a cross section view of the container and lid of FIG. 5, with a cyclone dirt bin positioned in the openable port, the cyclone dirt bin being in a closed configuration.
Figure 8:
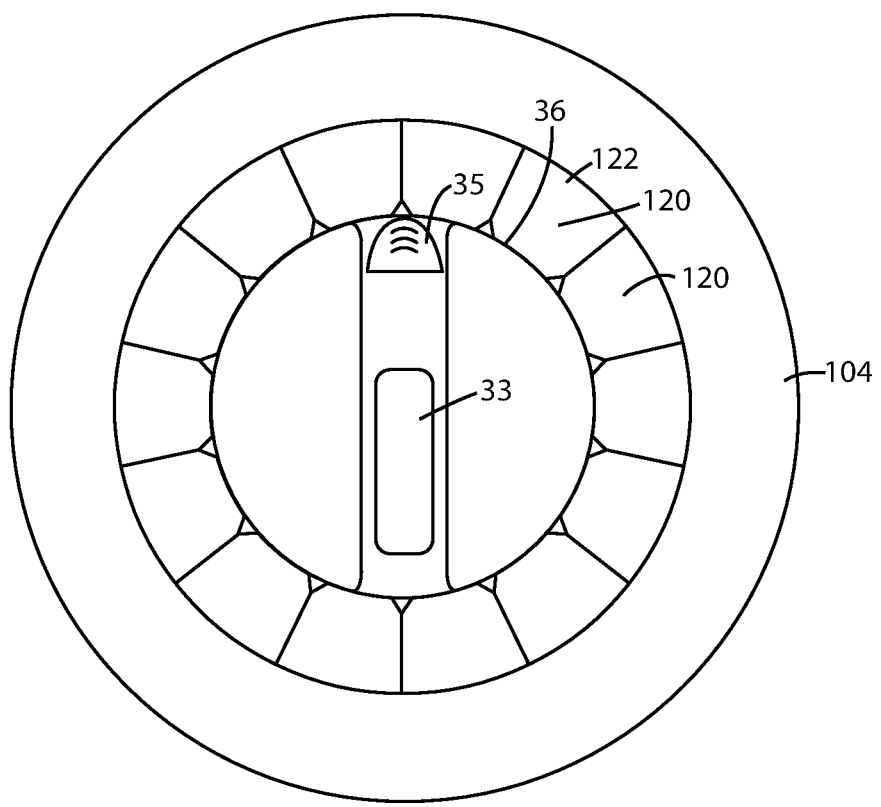
FIG. 8 is a top view of the lid of FIG. 1, with a cyclone dirt bin positioned in the openable port.

In FIGS. 6 and 8, a cyclone bin assembly 30 for a surface cleaning apparatus has been positioned in port 110. Cyclone bin assembly 30 includes an air treatment member, in this case a cyclone 31, and a dirt collection region 38 for collecting particulate matter dis-entrained from a dirty airflow by cyclone 31. A handle 33 is provided at an upper end 34 of the cyclone bin assembly. Cyclone bin assembly 30 has an openable lower end 32 releasably secured by a door closure member 37. A door release switch or actuator 35 is positioned external to the garbage can so it is operable by a user when the cyclone bin assembly 30 has been inserted into port 110 into an emptying position. Switch 35 is operatively connected to door closure member 37. As exemplified, switch 35 is provided adjacent handle 33 and is drivingly coupled to door closure member 37 via door actuator 39. It will be appreciated that switch 35 may be operatively connected to door closure member 37 by any other mechanical drive member or may be electrically connected thereto or wirelessly operatively connected thereto.

In the illustrated embodiment, inserting cyclone bin assembly 30 in port 110 results in flanges 120 being deflected towards the lower end 22 of container 20 by contact with the cyclone bin assembly 30. At least the inner ends 124 of each flange 120 are displaced into the interior volume 28 of container 20. Preferably, flanges 120 are configured such that at least a portion of each inner end 124 remains in contact or proximate an outer sidewall 36 of cyclone bin assembly 30, thereby forming at least a substantial if not a complete seal about cyclone bin assembly 30, to inhibit or prevent dust, allergens, and other particulate matter from exiting container 20. Optionally, if port 110 is sized to be slightly larger in diameter that the cyclone bin assembly or the dirt collection region inserted into port 110, then flanges 120 may contact most of the perimeter of the cyclone bin assembly or the dirt collection region.

Figure 7:
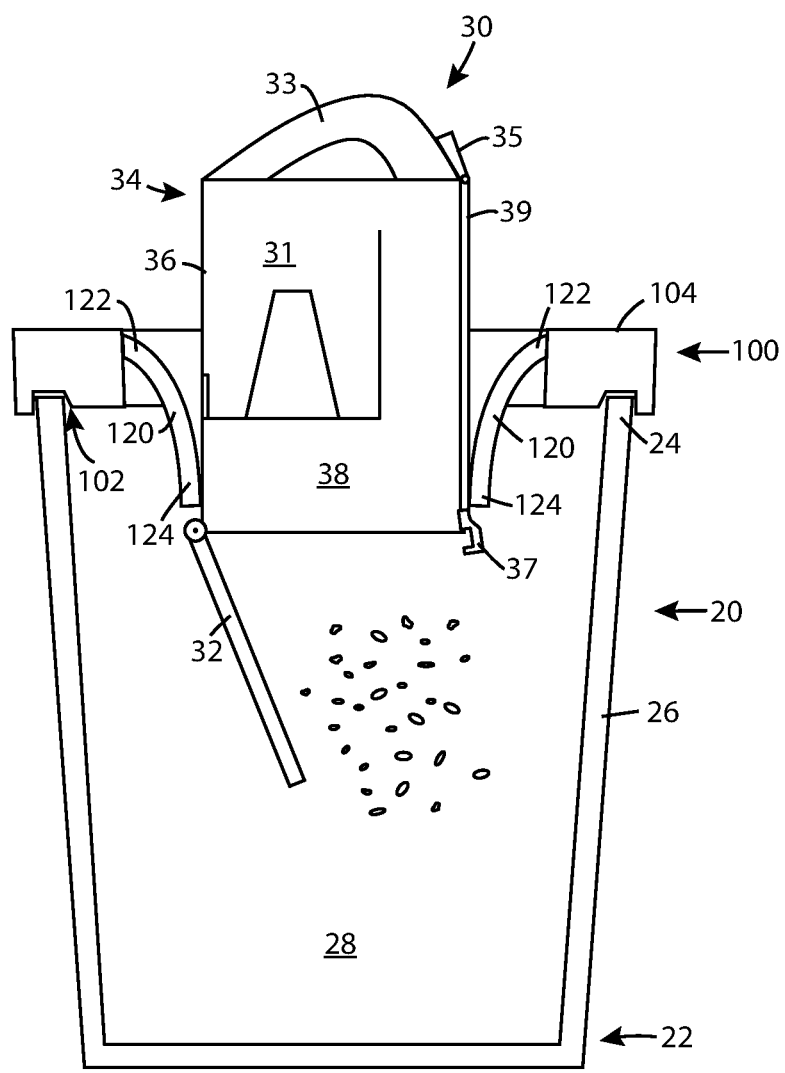
FIG. 7 is a cross section view of the container and lid of FIG. 5, with a cyclone dirt bin positioned in the openable port, the cyclone dirt bin being in an open configuration.

In FIG. 7, openable lower end 32 of cyclone bin assembly 30 has been moved into an open position. For example, door release switch 35 may have been deflected or rotated (e.g. by a user's thumb), resulting in a deflection or rotation of door closure member 37, whereby openable lower end 32 was released and moved to an open position, e.g. due to gravity or one or more biasing members (not shown).

As discussed previously with reference to FIG. 6, lid 100 and the substantial if not complete seal provided by flanges 120 about the outer sidewall 36 of cyclone bin assembly 30 may act to inhibit or prevent dust, allergens, and other particulate matter from exiting container 20 during transfer of such particles from dirt collection region 38 to the interior volume 28 of container 20.

Figure 9:
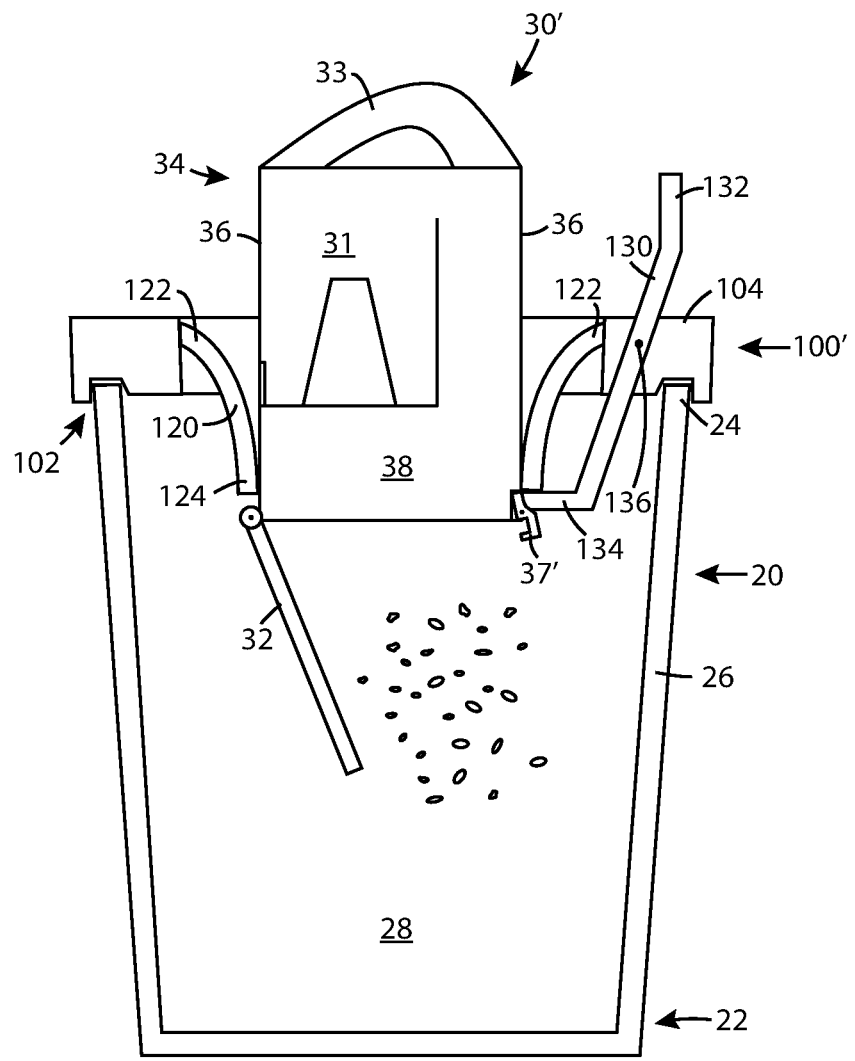
FIG. 9 is a cross section view of a container and lid according to another embodiment, with a lid actuator drivingly connected to a door actuator of a cyclone dirt bin positioned in an openable port of the lid.

FIG. 9 exemplifies an alternative embodiment of a lid, referred to generally as 100', with an alternative design of cyclone bin assembly 30' positioned in port 110 of lid 100'. The embodiment of lid 100' shown in FIG. 9 includes a lid actuator for actuating a door closure member of a cyclone bin assembly when the cyclone bin assembly has been positioned in port 110 of lid 100', but is otherwise similar to lid 100 shown in FIG. 7.

In the example cyclone bin assembly 30' shown in FIG. 9, a door release switch need not be provided proximate the upper end of the cyclone bin assembly. Instead, the door closure member 37' may be configured to be moved, e.g., deflected or rotated once the cyclone bin assembly has been inserted into port 110, thereby releasing openable lower end 32 into a closed or essentially closed volume. Otherwise, the example cyclone bin assembly 30' shown in FIG. 9 is similar to cyclone bin assembly 30 shown in FIG. 7.

As exemplified in FIG. 9, when cyclone bin assembly 30' is positioned in port 110, flanges 120 are configured such that at least a portion of each inner end 124 remains in contact or proximate an outer sidewall 36 of cyclone bin assembly 30', thereby forming at least a substantial if not a complete seal about cyclone bin assembly 30', to inhibit or prevent dust, allergens, and other particulate matter from exiting container 20. However, in this illustrated configuration the door closure member 37' is positioned below flanges 120, which may inhibit or prevent a user from releasing openable lower end 32 when cyclone bin assembly 30' is positioned in port 110. To address this potential issue, lid 100' is provided with a lid actuator 130.

Lid actuator 130 has an upper end 132 operable by a user from the exterior of the refuse container. As exemplified, lid actuator 130 projects upwardly from, e.g., top surface 104 of lid 100', and a lower end 134 is positioned in the interior volume 28 and below the lower surface 102 of lid 100'. In the illustrated example, lid actuator is pivotally secured to lid 100' by a shaft or other pivoting coupling 136. In this arrangement, the upper end 132 of lid actuator 130 may be manipulated by a user to cause the lower end 134 to drivingly engage and thereby actuate the door closure member 37' of cyclone bin assembly 30' to release openable lower end 32 when the bin assembly has been positioned in port 110.

Alternatively, the lid actuator may be of any other suitable configuration, including, for example a configuration in which the actuator is provided in a sidewall of the garbage can and inwardly slideable to actuate door closure member 37'.

It will be appreciate that in this aspect, and other aspects, of this disclosure cyclone bin assembly 30 may be of any design and may be an air treatment member of any type and need not be cyclonic. Further, instead of inserting part or all of an air treatment member (such as cyclone bin assembly 30) into port 110, the dirt collection region may comprise a dirt collection chamber that is external to the air treatment member, e.g., a cyclone chamber, and the dirt collection region may be removed from the rest of the air treatment member and part of all of it may be inserted into port 110 in order to empty the dirt collection chamber.

Refuse Container with Sub-Atmospheric Pressure Mode

The following is a general description of a refuse container having a suction source and other features set out herein that may be used by itself or in combination with one or more embodiments disclosed herein, including one or more of a lid for a refuse container having an openable port, dust control systems for refuse containers or surface treatment apparatus, and dust treatment systems for refuse containers or surface treatment apparatus. The following description contains various features of a refuse container having a suction source which may be used individually or in any combination or sub-combination.

In accordance with this aspect, a sub atmospheric is used to inhibit, substantially prevent or essentially prevent a dust plume of lighter dirt particles forming in the ambient air when the dirt collection region is emptied. For example, a suction motor may be used to draw air from the interior of a refuse container or the ambient air above or immediately above the refuse container. This will create a flow of air, e.g., into the refuse container if the suction motor is in communication with the interior of the refuse container, or into one or more inlet ports if the suction motor is in communication with the air above the refuse container, which may partially or substantially entrain the lighter dust that would otherwise form a dust plume. Accordingly, a smaller dust plume or essentially no dust plume may be formed.

Figure 11:
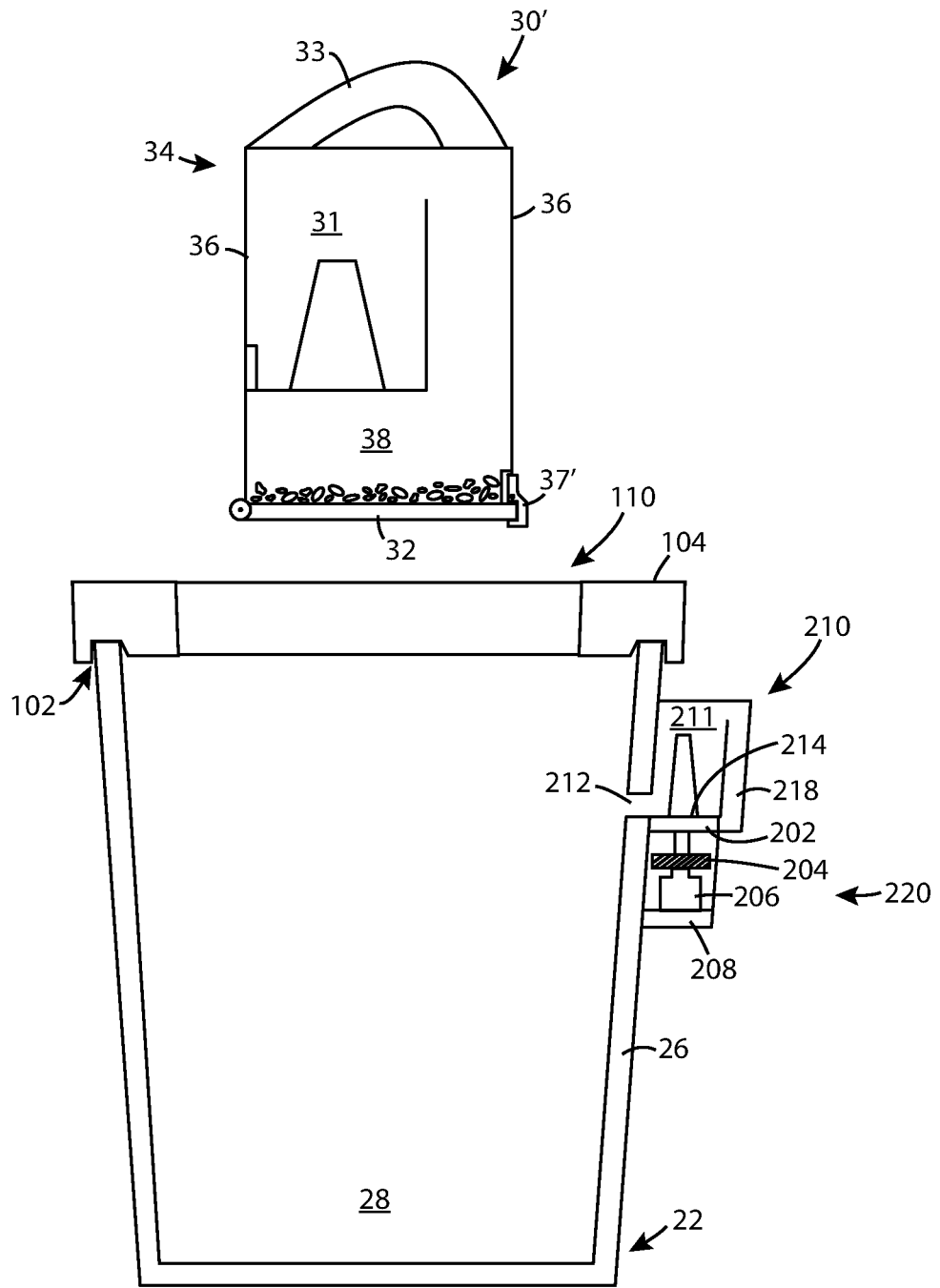
FIG. 11 is a cross section view of the container and first lid of FIG. 10, taken along line 11-11, with a cyclone dirt bin positioned above the container, the cyclone dirt bin being in a closed configuration.
Figure 12:
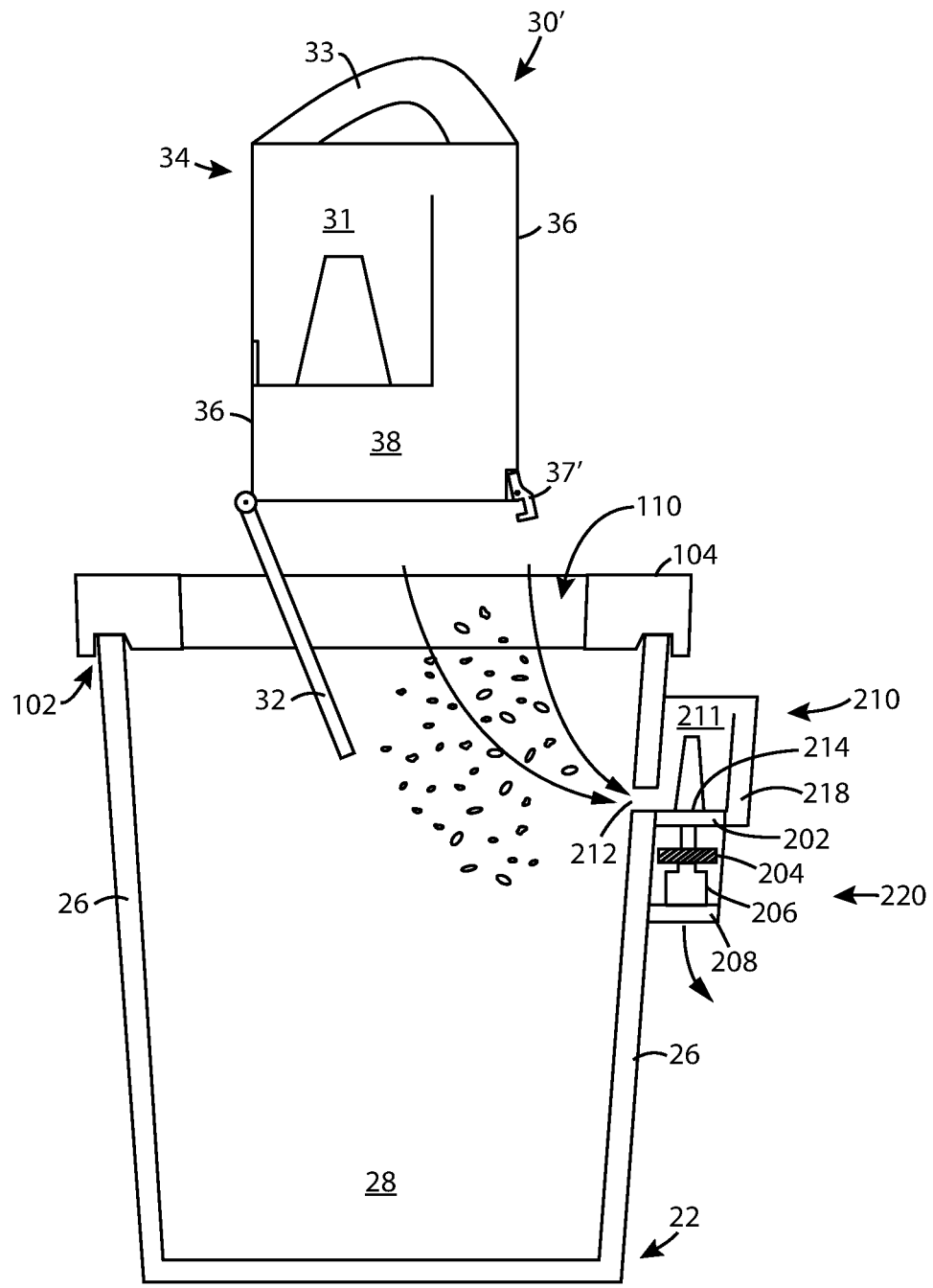
FIG. 12 is a cross section view of the container and first lid of FIG. 11, with the cyclone dirt bin in an open configuration, and with the suction source drawing air from the interior volume of the container.

In the examples illustrated in FIGS. 10-12, a suction source, referred to generally as 220, is provided on the refuse container and may be permanently mounted thereto or may be removable mounted. In the latter case, the suction source may be removed before a garbage can is taken to, e.g., the end of a drive way to be emptied into a garbage truck. By providing a suction source to draw air from the interior volume of the refuse container, some or all of a plume of fine dust or other particles generated during the emptying of a dirt collection region of a surface cleaning apparatus may be drawn into the interior of the refuse container, which may result in a more controlled transfer of the contents of the dirt collection region to the refuse container. By making the suction source 220 removable, damage to suction source 220 may be avoided when the garbage can is emptied.

Suction source 220 includes a suction motor 206 drivingly connected to a suction fan 204 for drawing air from the interior volume 28 of container 20, either directly or via an optional air treatment member 210. An optional pre-motor filter 202 is shown upstream of suction motor 206, and an optional post-motor filter 208 is shown downstream of suction motor 206 and upstream of a clean air outlet. It will be appreciated that one or both of these filters may not be provided in alternative embodiments.

In the illustrated configuration, an upstream or inlet end of suction source 220 is in airflow communication with the interior volume 28 via an inlet 212 provided in the sidewall 26 of container 20. An optional air treatment member 210 is provided downstream of inlet 212. In the illustrated example, air treatment member 210 is a cyclonic air treatment member, and has a cyclone 211 in fluid communication with the interior volume 28 of container 20 via inlet 212. A dirt collection region 218 is provided to collect particles dis-entrained from air drawn through inlet 212 by cyclone 211. Air treatment member 210 also has an outlet 214 in fluid communication with suction fan 204. Alternatively, or additionally, the air treatment member may comprise a bag, a filter, an additional cyclonic cleaning stage and/or other air treatment known in the art.

In the illustrated examples, inlet 212 is provided proximate the upper end 24 of container 20. Alternatively, inlet 212 may be provided proximate the lower end 22 of container 20, or between the upper and lower ends 24, 22.

Also, in the illustrated examples a single inlet 212 is provided. Alternatively, two or more inlets 212 may be provided. In some embodiments, a manifold may be provided between two or more inlets 212 and the suction fan 204. For example, two or more inlets 212 may converge at or before the inlet to optional air treatment member 210.

The operation of suction source 220 in controlling dust, allergens, and other particulate matter when emptying a dirt collection region of a surface cleaning apparatus will now be discussed with reference to FIGS. 11 and 12.

In FIG. 11, a cyclone bin assembly 30' for a surface cleaning apparatus has been positioned above port 110. For example, a user may have detached and carried such a dirt collection region to such a position. Alternatively, if the surface cleaning apparatus is a hand vacuum cleaner, then the entire hand vacuum cleaner may be so positioned. Cyclone bin assembly 30' includes a dirt collection region 38 for collecting particulate matter dis-entrained from a dirty airflow by an air treatment member, in this case a cyclone 31.

In FIG. 12, openable lower end 32 of cyclone bin assembly 30' has been moved into an open position. For example, a user may have opened the dirt collection region, with the expectation that gravity would transfer at least the bulk of the contents of the dirt collection region to the interior of the refuse container. For example, door closure member 37' may have been deflected or rotated (e.g. by a user's thumb), whereby openable lower end 32 was released and moved to an open position, e.g. due to gravity or one or more biasing members (not shown).

As discussed previously, opening the dirt collection region 38 for emptying often results in a cloud or plume of fine dust or other particles billowing outwards from the opening of the dirt collection region and/or from the container 20 into which the dirt collection region is being emptied. The particles in such a plume or cloud may be dispersed during the emptying process, resulting in a less than complete transfer from the dirt collection region 38 to the interior 28 of the refuse container 20. This may be considered undesirable by a user, particularly if the plume or cloud contains dust or other allergens to which the user is sensitive.

To address this potential issue, in FIG. 12 suction motor 206 has been actuated to drive suction fan 204, resulting in an airflow from the interior volume 28 of container 20, through inlet 212 and optional air treatment member 210, and through post-motor filter 208 to an area exterior of the container 20. Advantageously, this may result in some or all of any particles dispersed in a plume or cloud following the opening of dirt collection region 38 being drawn into the interior volume 28 of container 20 and/or into air treatment member 210. Accordingly, the amount of dust, allergens, or other fine particulate matter that is 'lost' (i.e. is not transferred to container 20 or to air treatment member 210) during the emptying of dirt collection region 38 into container 20 may be reduced or eliminated.

Figure 13A:
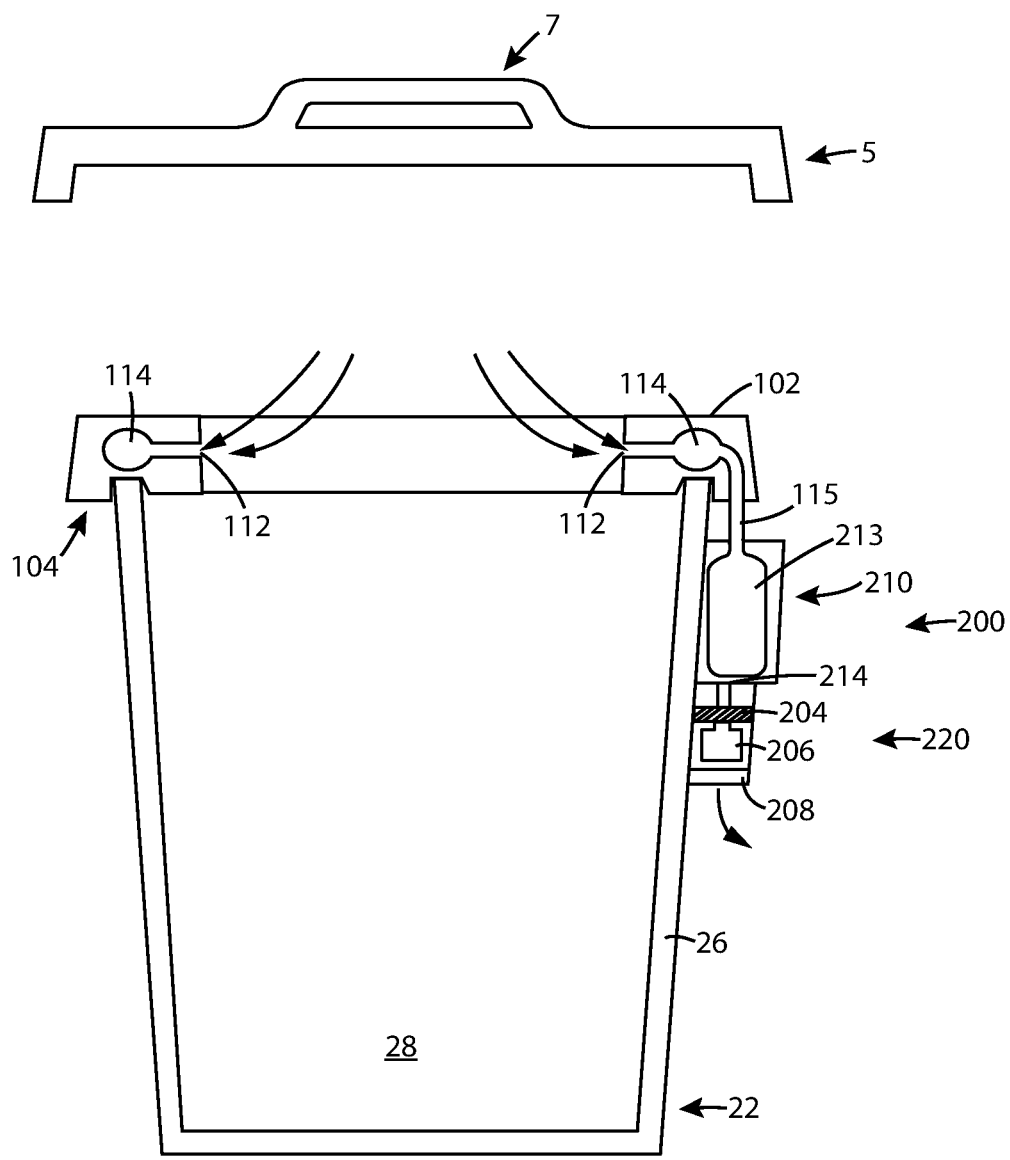
FIG. 13A is a cross section view of a container, a first lid having an open port and a suction source, and a second lid in a removed position in accordance with another embodiment.
Figure 13B:
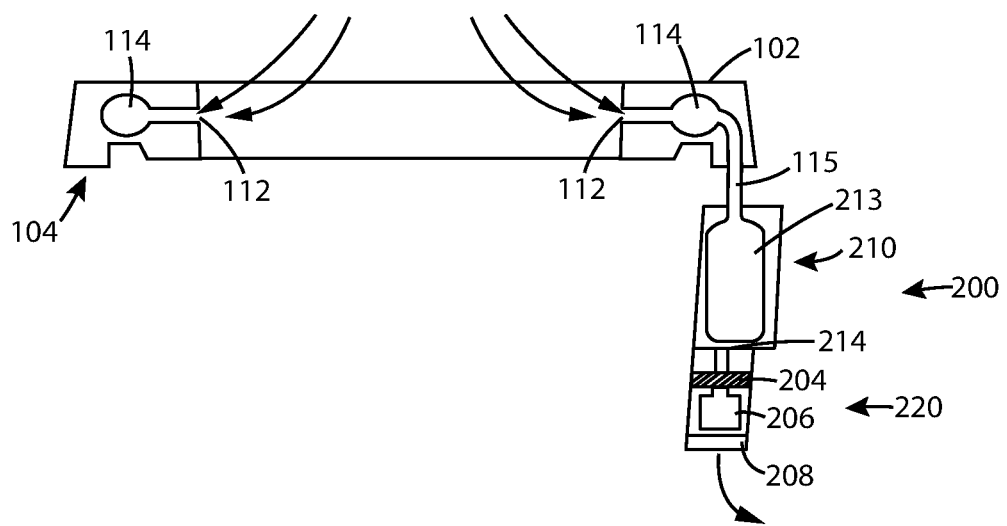
FIG. 13B is a cross section view of the first lid and suction source of FIG. 13A.
Figure 14:
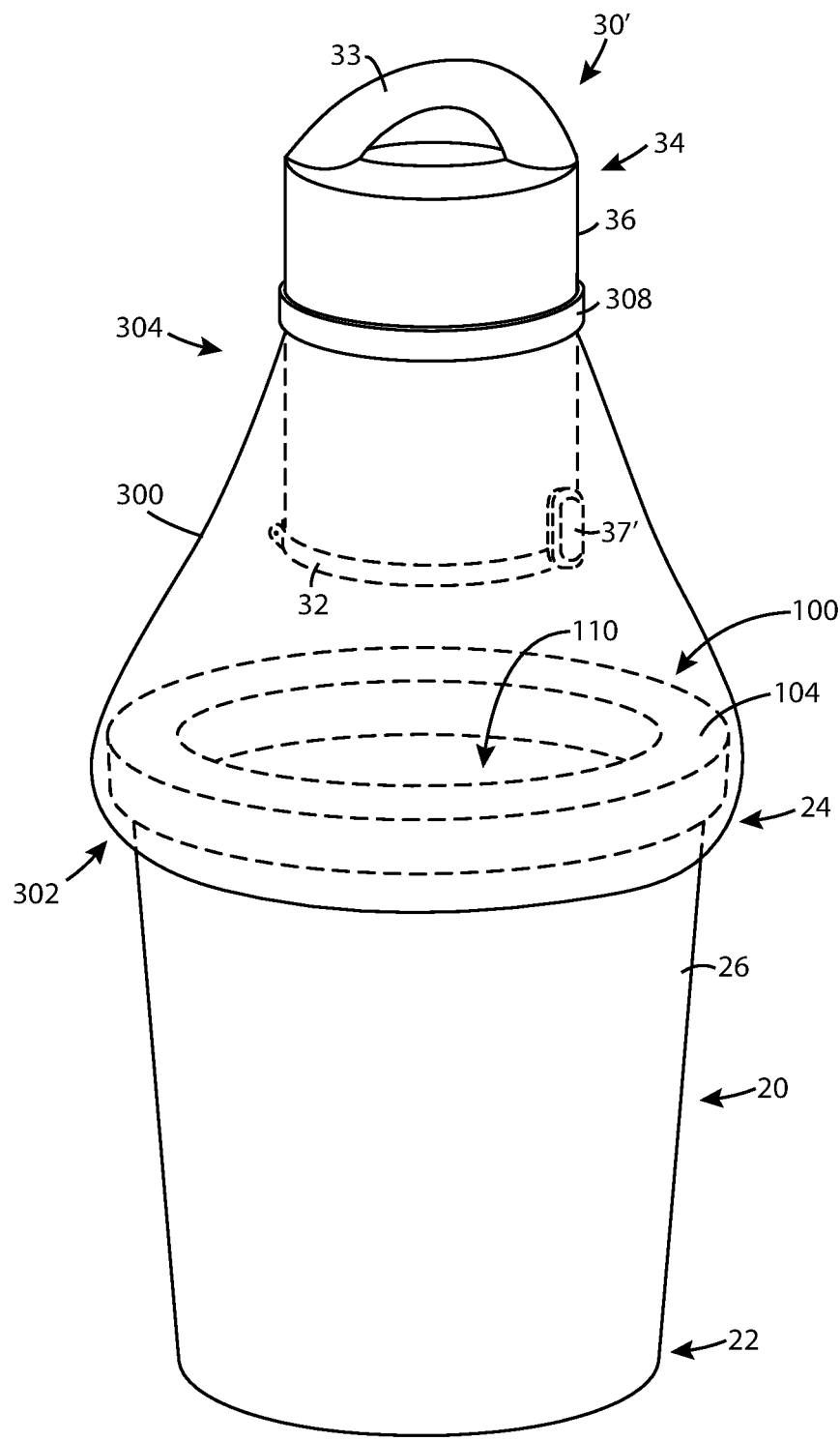
FIG. 14 is a perspective view of a container, a first lid having an open port, and a cyclone bin assembly having a deployable closure member in accordance with one embodiment.

FIGS. 13A and 13B illustrate an alternative embodiment in which a suction source 220 is provided on the first or inner lid 100 for a refuse container 20. In the illustrated example, suction source 220 includes a suction motor 206 drivingly connected to a suction fan 204 for drawing air from inlets 112 located about the perimeter of port 110 in lid 100. A pre-motor filter 202 and a post-motor filter 208 are also shown upstream and downstream, respectively, of suction motor 206, although it will be appreciated that one or both of these filters may not be provided in alternative embodiments.

In FIG. 13A, a second or upper lid 5 is also shown in a removed position. Upper lid 5 is configured to rest on or engage with the upper surface 104 of lid 100, such that the second lid 5 overlies all or substantially all of port 110.

In the illustrated configuration, inlets 112 are provided on an inner surface of port 110 between the upper surface 104 and a lower surface 102 of lid 100. An optional air treatment member 210 is provided downstream of inlets 112. In the illustrated example, air treatment member 210 includes a vacuum bag 213 for collecting particles from a dirty airflow into the bag, as is known in the art. Air treatment member 210 is in fluid communication with a conduit 115 that is downstream of an annular manifold 114 provided about port 110. Downstream portions of inlets 112 are connected to manifold 114, providing a fluid flow path from inlets 112 to air treatment member 210. Air treatment member 210 also has an outlet 214 in fluid communication with suction fan 204. Alternatively, the air treatment member can comprise a cyclone, a filter, an additional cyclonic cleaning stage and/or other air treatment known in the art.

In the illustrated example, inlets 112 are provided on an inner surface of port 110. Alternatively, inlets 112 may be provided on the lower surface 102 of lid 100, or on the upper surface 104 and may optionally extend above upper surface 104.

Also, in the illustrated example two inlets 112 are provided. Alternatively, three or more inlets 112 may be provided, or a single inlet 112 may be provided.

Also, in the illustrated example, an annular manifold 114 is provided between inlets 112 and the air treatment member 210. Alternatively, each inlet 112 may be provided with a dedicated conduit to optional air treatment member 210.

Also, as illustrated in FIG. 13B, suction source 200 is provided on lid 100. For example, second lid 5 and container 20 (as shown in FIG. 13A) may have been purchased or otherwise acquired as a set, and first or inner lid 110 shown in FIG. 13B may be acquired as an option or a retrofit (e.g. acquired separately) to provide the suction source to effect a more controlled transfer of the contents of the dirt collection region to the refuse container. Suction source 200 may be secured to lid 100 in any suitable manner. For example, suction source 200 and/or optional air treatment member 210 may be removably mounted to lid 100, e.g. an upper end of conduit 115 may be threaded to provide for rotational engagement and disengagement with corresponding threads in lid 100. Alternatively, suction source 200 and/or optional air treatment member 210 may be non-removably (e.g. integrally formed with) mounted to lid 100.

Also, in the illustrated examples, suction source 200 is provided on lid 100. Alternatively, suction source 200 may be provided on the exterior of container 20. Suction source 200 may be secured to container 20 in any suitable manner. For example, suction source 200 and/or optional air treatment member 210 may be removably mounted to container 20. Alternatively, suction source 200 and/or optional air treatment member 210 may be non-removably (e.g. integrally formed with) mounted to container 20.

Also, in the illustrated examples, suction source 200 is configured to be positioned on the exterior of container 20. Alternatively, suction source 200 and/or optional air treatment member 210 may be positioned (e.g. removably or non-removably) in the interior of container 20.

It will be appreciated that the lid may include the openable port of the aspect discussed previously and the air may be drawn for a substantially sealed interior 28 of container 20.

Alternatively or in addition, it will be appreciated that the suction source may be actuated prior to, upon or subsequent to the opening of the dirt collection region. For example, if port 110 is provided with flanges, then the suction source may be actuated when the flanges commence deflection upon opening of the port. Alternatively, a sensor, e.g., an infra-red (IR) sensor, may be provided to actuate the suction source when the dirt collection region is brought proximate to or into the container 20.

Cyclone Bin Assembly with Deployable Closure Member

The following is a general description of a cyclone bin assembly having a deployable closure member and other features set out herein that may be used by itself or in combination with one or more embodiments disclosed herein, including one or more of a lid for a refuse container having an openable port, dust control systems for refuse containers or surface treatment apparatus, dust treatment systems for refuse containers or surface treatment apparatus, and a refuse container having a suction source. The following description contains various features of a cyclone bin assembly having a deployable closure member that may be used individually or in any combination or sub-combination.

In accordance with this aspect, a flexible closure member or hood is provided to create a closed or substantially closed volume between the interior of container 20 and the openable portion of the dirt collection region. Accordingly, when the dirt collection region is opened, even if the finer dirt creates a plume or cloud, the plume or cloud is contained or substantially contained thereby reducing or preventing the loss of finer particulate matter upon emptying the dirt collection region.

As exemplified in FIGS. 14-17, a flexible closure member 300 is shown in association with a cyclone bin assembly for a surface cleaning apparatus. In the example shown in FIGS. 14 and 17, cyclone bin assembly 30' includes an air treatment member, in this case a cyclone 31, and a dirt collection region 38 for collecting particulate matter dis-entrained from a dirty airflow by cyclone 31. A handle 33 is provided at an upper end 34 of the cyclone bin assembly. Cyclone bin assembly 30' has an openable lower end 32 releasably secured by a door closure member 37'. It will be appreciated that, as discussed previously, any air treatment member and openable dirt collection region known in the surface cleaning arts may be used.

As exemplified, flexible closure member 300 is mounted on or secured to an outer sidewall 36 (i.e. an exterior surface) of cyclone bin assembly 30'. In the illustrated example, a first or upper end 304 is secured to sidewall 36. An optional shroud 308 is provided about the sidewall 36. Shroud 308 may assist in retaining or gathering flexible closure member 300 when it is in a retracted position. It will be appreciated that flexible closure member 300 may be permanently mounted or removably mounted to any portion of the dirt collection region, air treatment member, or surface cleaning apparatus.

Flexible closure member 300 comprises a pliant, flexible material, and may be provided as a single piece construction (e.g. having an annular or conical shape), or may alternatively be provided as two or more panels of material.

Preferably, flexible closure member 300 comprises at least one of a plastic material (e.g. a polyethylene film, a bioplastic film, and the like) and a natural fabric (e.g. cotton, hemp, and the like). In one or more preferred embodiments, flexible closure member 300 may be made from a substantially or completely air-impermeable material.

Flexible closure member 300 is preferably transparent or translucent, although it will be appreciated that all or a portion of flexible closure member 300 may be opaque.

Flexible closure member 300 preferably has a length sufficient to permit a user to hold, e.g., bin assembly 30' while standing upright, while flexible closure member is secured to container 20 and while emptying the dirt collection region.

Figure 15:
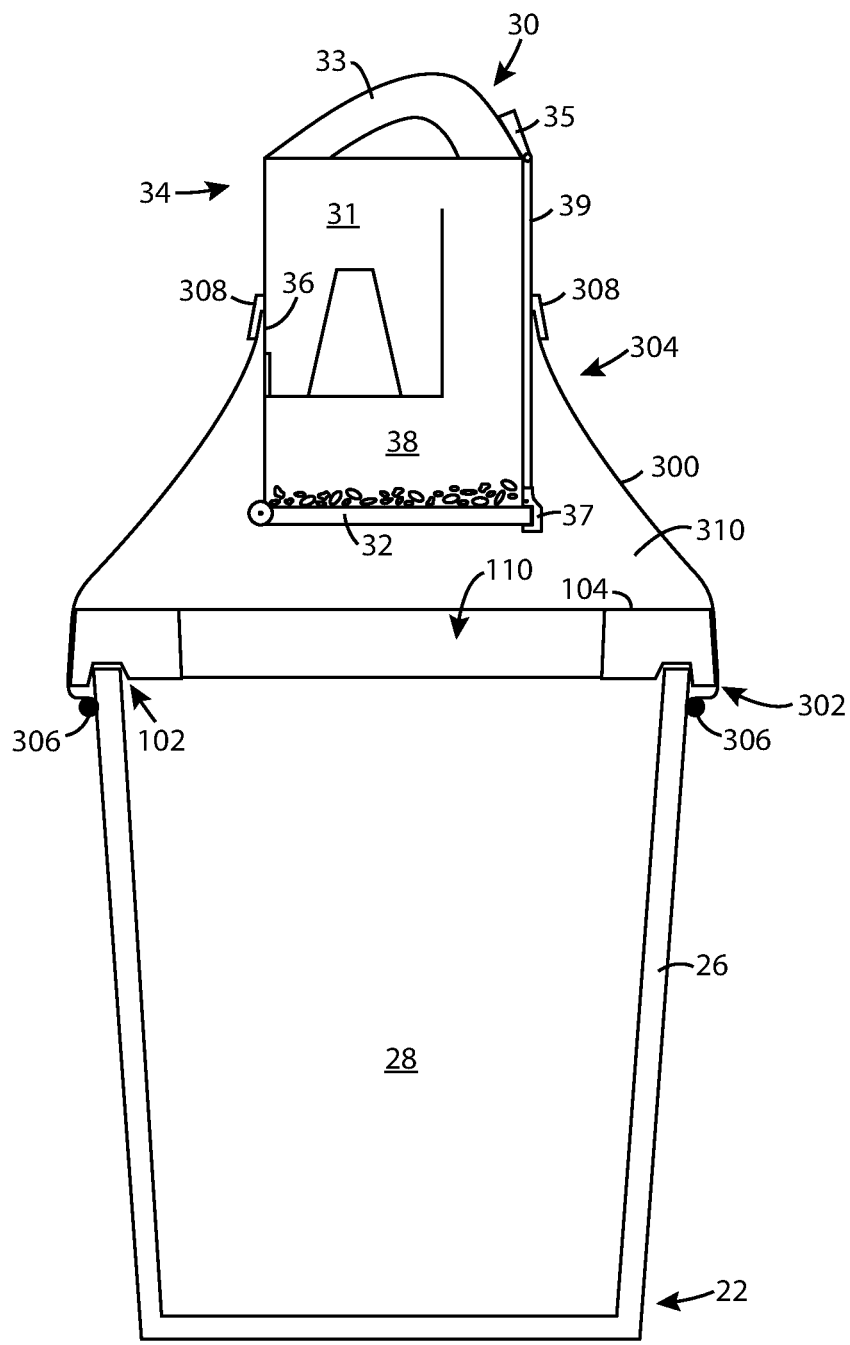
FIG. 15 is a cross section view of a container, a first lid having an open port, and a cyclone bin assembly having a deployable closure member in accordance with another embodiment, the cyclone bin assembly being in a closed configuration.

As exemplified in FIG. 15, a securing member 306 may be provided at or proximate a second or lower end 302 of flexible closure member 300. Securing member 306 is configured to assist in retaining the lower end 302 of flexible closure member 300 in a position where the flexible closure member encloses upper end 24 of refuse container 20.

In a preferred embodiment, securing member 306 may comprise an elongate elastic member extending about all or a portion of a perimeter of lower end 302 of flexible closure member 300. In such an arrangement, securing member 306 may assist in providing a partial or complete seal between lower end 302 of flexible closure member 300 and sidewall 26 of refuse container 20. Preferably, such an elastic member has sufficient elasticity so as to be stretched from a length approximately equal to the circumference of an outer perimeter of the cyclone bin assembly, to a length approximately equal to a circumference of an outer perimeter of a refuse container 20 or of a lid 100.

In another preferred embodiment, securing member 306 may comprise a drawstring extending about all or a portion of a perimeter of lower end 302 of flexible closure member 300. Preferably, such a drawstring can be extended to a length approximately equal to a circumference of an outer perimeter of a refuse container 20 or of a lid 100, and retracted to a second length approximately equal to the circumference of an outer perimeter of the cyclone bin assembly.

For example, in a retracted position (not shown), lower end 302 of flexible closure member 300 may be gathered or otherwise positioned under shroud 308, such that all or substantially all of flexible closure member 300 is positioned between shroud 308 and sidewall 36. Preferably, in such a position securing member 306 may be used to secure lower end 302 to the cyclone bin assembly (e.g. to sidewall 36).

In another preferred embodiment, flexible closure member 300 may itself be sufficiently resilient or elastic such that a securing member 306 is not required.

Alternatively, or in addition, container 20 may be provided with a locking member to which the lower end of flexible closure member 300 is releasably attachable. For example, the lower end of flexible closure member 300 and the garbage can may have male and female interengageable hook and loop fasteners.

The operation of flexible closure member 300 in controlling dust, allergens, and other particulate matter when emptying a dirt collection region of a surface cleaning apparatus will now be discussed with reference to FIGS. 15 and 16.

In FIG. 15, a cyclone bin assembly 30 for a surface cleaning apparatus has been positioned above port 110 of container 20 or may be above an open top of container 20. For example, a user may have detached and carried the cyclone bin assembly to such a position. Cyclone bin assembly 30 includes a dirt collection region 38 for collecting particulate matter dis-entrained from a dirty airflow by an air treatment member, in this case a cyclone 31.

Also, in FIG. 15 flexible closure member 300 has been moved to a deployed position, in which lower end 302 has been positioned around upper portion 24 of container 20, and optionally retained in such a position by optional securing member 306. As a result, an enclosed volume 310 (i.e. a closed volume) defined by flexible closure member 300 extends between the upper end 304 of flexible closure member 300 and includes the interior volume 28 of container 20. Notably, openable lower end 32 of cyclone bin assembly 30 is positioned within enclosed volume 310.

Figure 16:
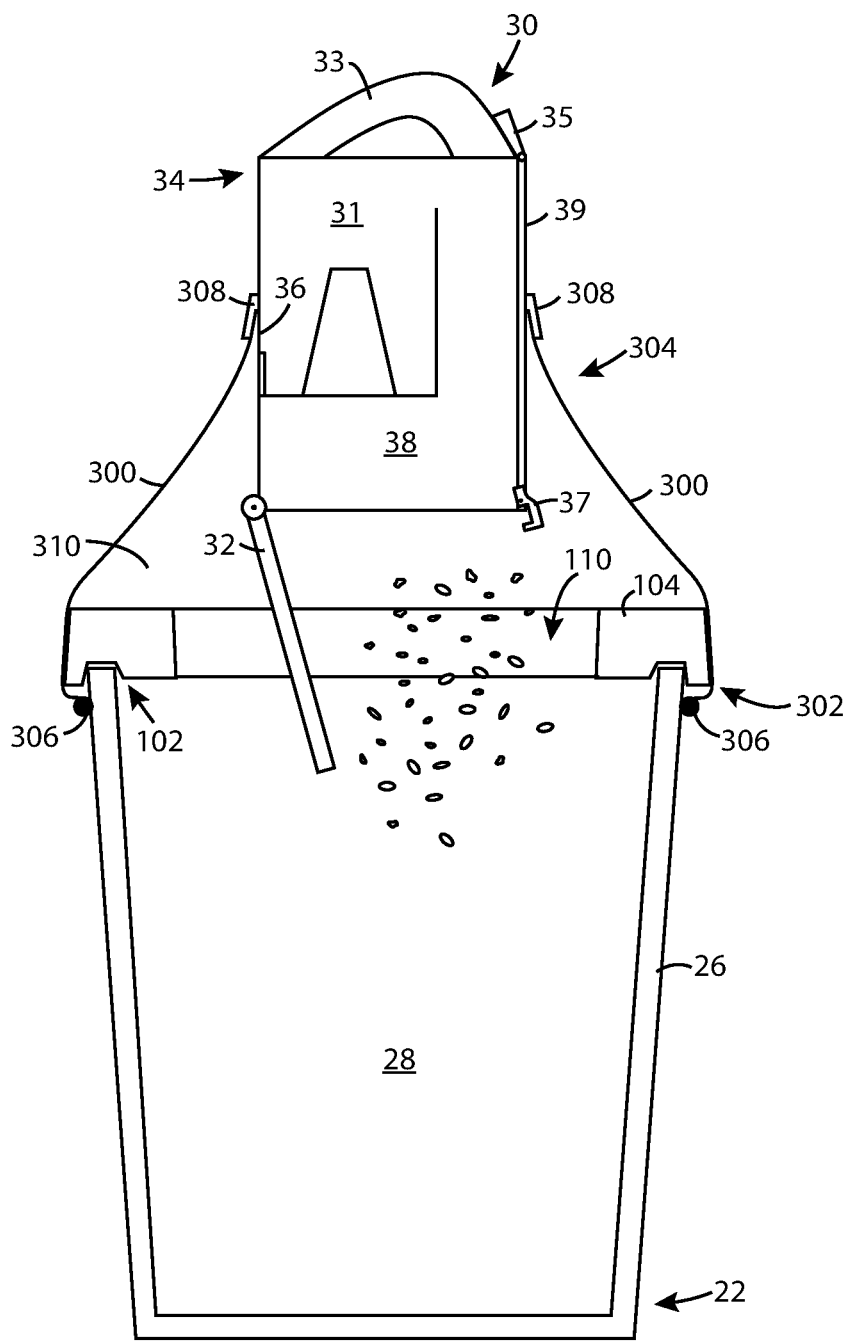
FIG. 16 is a cross section view of the container, first lid, cyclone bin assembly, and deployable closure member of FIG. 15, with the cyclone bin assembly in an open configuration.

In FIG. 16, openable lower end 32 of cyclone bin assembly 30 has been moved into an open position. For example, a user may have opened the dirt collection region, with the expectation that gravity would transfer at least the bulk of the contents of the dirt collection region to the interior of the refuse container. For example, door release switch 35 may have been deflected or rotated (e.g. by a user's thumb), resulting in a deflection or rotation of door closure member 37, whereby openable lower end 32 was released and moved to an open position, e.g. due to gravity or one or more biasing members (not shown).

As discussed previously, opening the dirt collection region 38 for emptying often results in a cloud or plume of fine dust or other particles billowing outwards from the opening of the dirt collection region and/or from the container 20 into which the dirt collection region is being emptied. The particles in such a plume or cloud may be dispersed during the emptying process, resulting in a less than complete transfer from the dirt collection region 38 to the interior 28 of the refuse container 20. This may be considered undesirable by a user, particularly if the plume or cloud contains dust or other allergens to which the user is sensitive.

Advantageously, in the configuration illustrated in FIG. 16, flexible closure member 300 may act to direct some or all of any particles dispersed in a plume or cloud following the opening of dirt collection region 38 towards the interior volume 28 of container 20. Accordingly, the amount of dust, allergens, or other fine particulate matter that is dispersed during the emptying of dirt collection region 38 into container 20 may be reduced or eliminated.

As discussed previously, the actuator to open the dirt collection region may be located so that it may be actuated when flexible closure member is deployed, e.g., it is located at a position exterior to enclosed volume 310. Accordingly, as exemplified in FIGS. 15 and 16, cyclone bin assembly 30 is provided with a door release switch 35 (positioned adjacent handle 33) that is operatively coupled to door closure member 37 via door actuator 39. In such a configuration, i.e. in which the actuator 35 for the openable door 32 is exterior to the closed volume 310 when the flexible closure member 300 is in the deployed position, the opening of openable door 32 may be relatively straightforward for a user. Any mechanism discussed herein may Alternatively be used.

Figure 17:
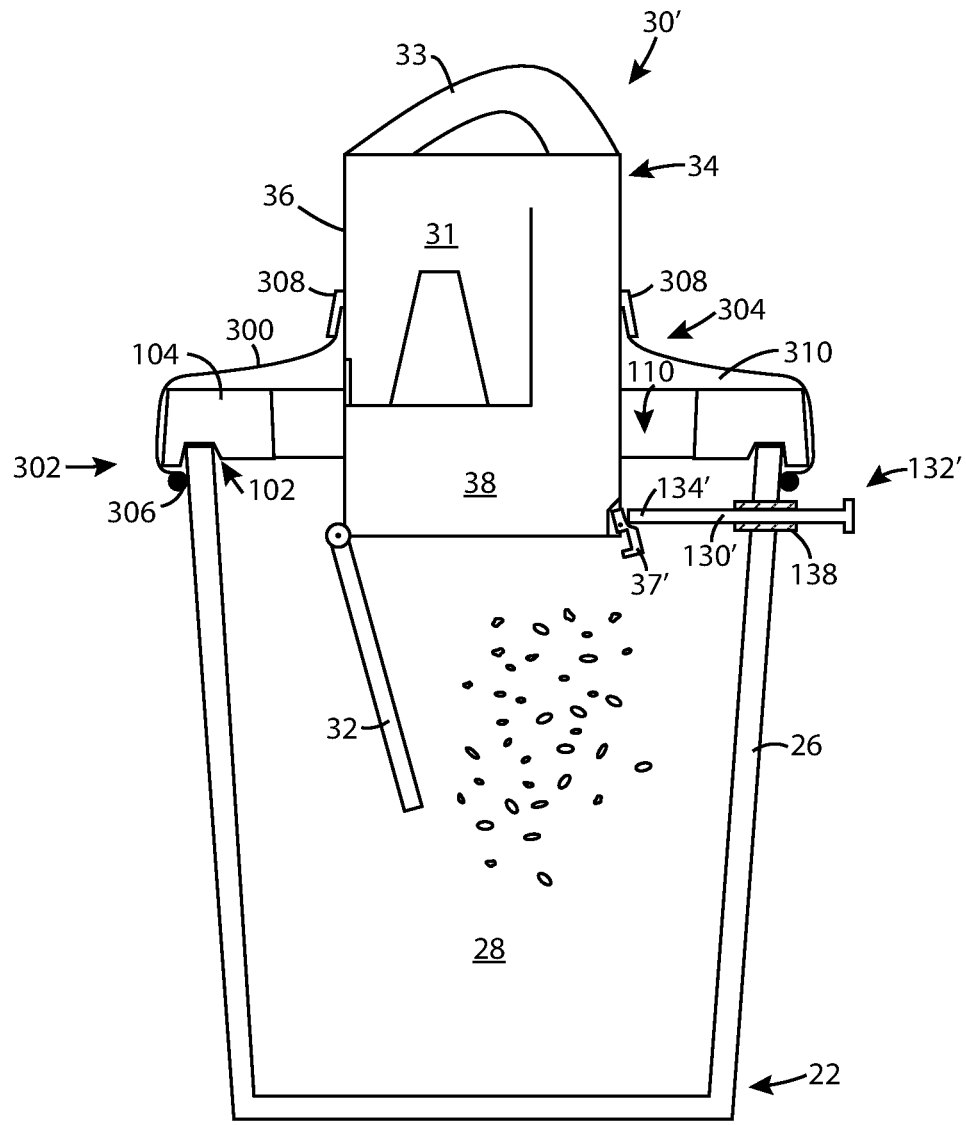
FIG. 17 is a cross section view of a container, a first lid having an open port, a cyclone bin assembly having a deployable closure member in accordance with another embodiment, the cyclone bin assembly being in an open configuration.

FIG. 17 illustrates an alternative embodiment of a refuse container 20, with an alternative design of cyclone bin assembly 30'. In the example cyclone bin assembly 30' shown in FIG. 17, a door release switch is not provided proximate the upper end of the cyclone bin assembly. Instead, the door closure member 37' is configured to be deflected or rotated directly, thereby releasing openable lower end 32.

As shown in FIG. 17, when lower end 32 of cyclone bin assembly 30' is positioned in interior volume 28 of container 20, and the flexible closure member 300 has been deployed about the upper end 24 of container 20, the door closure member 37' is positioned in the interior volume 310 provided by flexible closure member 300. In this illustrated configuration, the flexible closure member 300 may inhibit or prevent a user from releasing openable lower end 32. To address this potential issue, container 20 is provided with a release actuator 130'.

Release actuator 130' has a first portion 132' projecting generally outwardly from sidewall 26 of container 20, and a second portion 134' positioned in the interior volume 28. In the illustrated example, release actuator 130' is positioned in an annular opening in sidewall 26 such that the actuator may be translated inwardly or outwardly with respect to container 20. Preferably, a spring 138 or other biasing member is provided to bias the release actuator 130' towards a position in which the second portion 134' remains in interior volume 28, and in which first portion 132' remains exterior to container 20. In this arrangement, the first portion 132' of actuator 130' may be manipulated by a user to cause the second portion 134' to extend inwardly to drivingly engage and thereby actuate the door closure member 37' of cyclone bin assembly 30' to release openable lower end 32 when the flexible closure member 300 is in a deployed position. It will be appreciated that release actuator 130' may have any configuration and may be rotatable, translatable or otherwise moveably mounted. Also, release actuator 130' may communicate wirelessly with door closure member 37'.

It will be appreciated that any embodiment of this aspect may be used advantageously with an embodiment which creates a sub atmospheric pressure in interior volume 28 and/or interior volume 310.

Dust Control and/or Treatment for Refuse Container or Surface Treatment Apparatus The following is a general description of dust control and dust treatment systems for a refuse container or for a surface treatment apparatus and other features set out herein that may be used by itself or in combination with one or more embodiments disclosed herein, including one or more of a lid for a refuse container having an openable port, a refuse container having a suction source, a cyclone bin assembly having a deployable closure member, and a dirt collection region of a surface treatment apparatus having a sub-atmospheric pressure mode. The following description contains various features of dust control and dust treatment systems that may be used individually or in any combination or sub-combination.

In accordance with this aspect, a dust control system is provided for selectively directing a dust control agent towards an area in and/or above the interior volume of the refuse container, e.g. below a dirt emptying outlet of a dirt collection region of a surface treatment apparatus. By providing a dust control agent above the interior volume of the container, the dispersal of dust, allergens, or other fine particulate matter into the air, e.g. while particulate matter is being transferred from a dirt collection region of a surface cleaning apparatus to the refuse container, may be inhibited or prevented, which may result in a more controlled transfer of the contents of the dirt collection region to the refuse container. Alternatively, or additionally, the dust control system may be configured to selectively direct a dust control agent towards the interior volume of the refuse container.

Alternatively or in addition, in accordance with this aspect a dust treatment system is provided for selectively directing a dust treatment agent to, e.g., the interior volume of the refuse container and/or a dirt collection region and/or an air treatment member such as a cyclone chamber. Dust, dirt, and other refuse collected in the refuse container may result in the growth of undesirable organisms. Such organisms may have a negative effect of the air quality surrounding container 20. Accordingly, a refuse container 20 may include one or more treatment applicators that provide one or more treatment agents (e.g. disinfecting, sanitizing, and/or deodorizing agents) in the interior volume 28 to reduce or eliminate organisms and/or other odor sources in the interior volume of the container. Disinfecting agents may be any element or emission that may reduce or inhibit growth of organisms in interior volume 28, or that are harmful or lethal to organisms that may grow in interior volume 28. Examples include ultra-violet (UV) light, ozone ($O_3$), and hydrogen peroxide ($H_2O_2$). An advantage of this design is that it may reduce or eliminate potentially harmful organisms (e.g. allergens), or reduce or eliminate odors emanating from the collected refuse.

Figure 18:
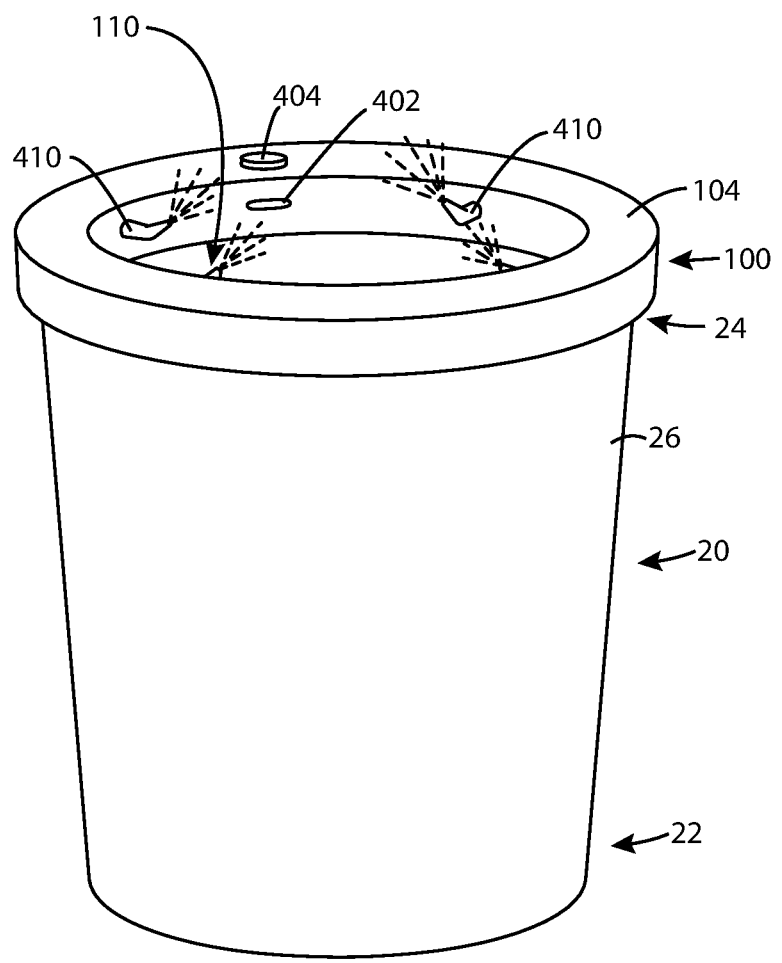
FIG. 18 is a perspective view of a container and a first lid having an open port and a dust control member providing a dust control agent according to one embodiment.
Figure 19:
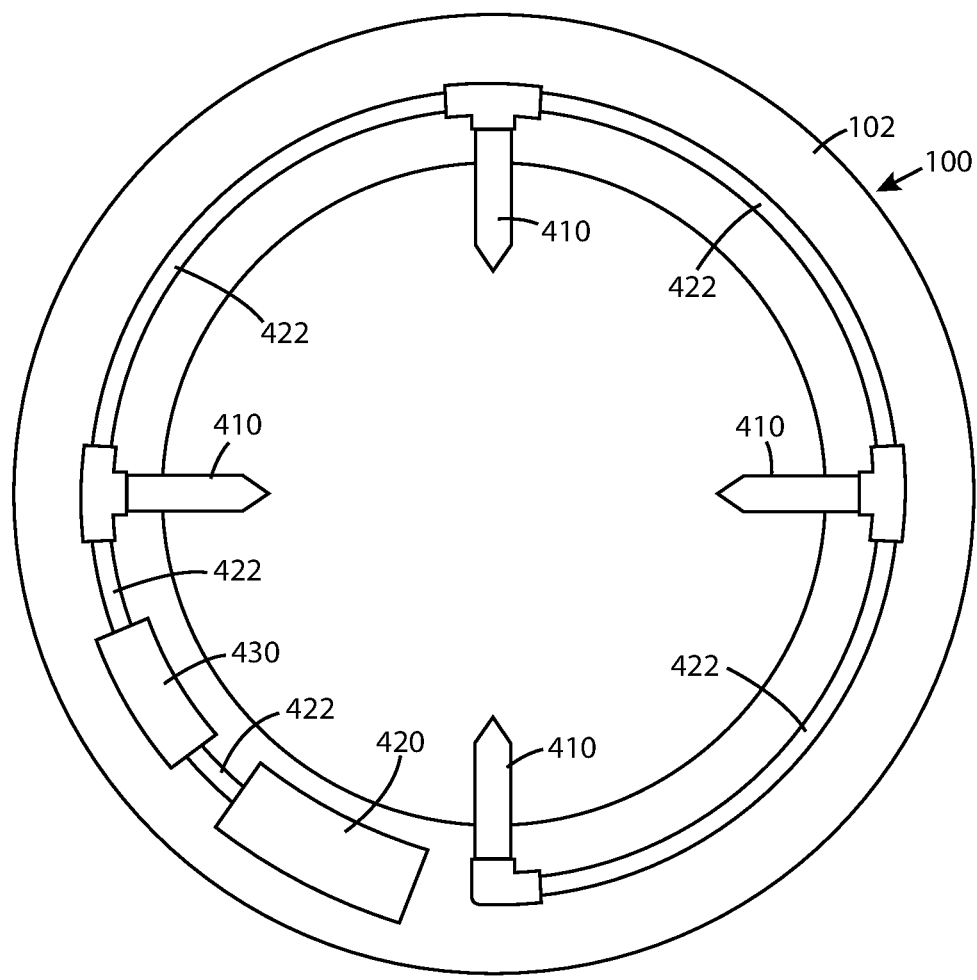
FIG. 19 is a bottom view of the lid of FIG. 18.

As exemplified in FIGS. 18 and 19, the dust control system includes a plurality of nozzles 410 for dispersing a liquid, e.g. water, into the air in the form of, e.g., a mist or other dispersion. Nozzles 410 may be provided on an inner surface of port 110 between the upper surface 104 and a lower surface 102 of lid 100. As exemplified in FIG. 19, the nozzles 410 are in fluid communication via conduit 422 with a fluid pump 430 that is itself in fluid communication with a reservoir 420. Reservoir 420 is configured to store a liquid to be dispersed (e.g. water).

It will be appreciated that the liquid, e.g., water, may be dispersed using any means known in the arts, such as an ultrasonic nebulizer or the like.

In the illustrated example, nozzles 410 are provided on an inner surface of port 110. Alternatively, or additionally, nozzles 410 may be provided on the upper surface 104 of lid 100, or on the lower surface 102, or on container 20 itself.

Also, in the illustrated example four nozzles 410 are provided. Alternatively, five or more nozzles 410 may be provided, or three or two or only one nozzle 410 may be provided.

Also, in the illustrated example, nozzles 410 are connected in series using conduit 422. Alternatively, each nozzle 410 may be provided with a dedicated conduit to pump 430.

It will be appreciated that the dust control system may be actuated in a number of ways and any method discussed herein for actuating a suction motor to produce sub atmospheric pressure may be used.

For example, in the configuration illustrated in FIG. 18, a first dust control system actuator 404, in this example a depressible button, is provided on upper surface 104 of lid 100. Pump 430 may be configured to direct fluid from reservoir 420 to nozzles 410 in response to actuator 404 being depressed. Alternatively, pump 430 may be configured to direct fluid to nozzles 410 after a pre-determined delay period following the depression of button 404.

Alternatively, or in addition, a second dust control system actuator 402, a sensor such as an infra-red (IR) sensor, may be provided, e.g., on an inner surface of port 110 between the upper surface 104 and a lower surface 102 of lid 100. IR sensor 402 is preferably configured to detect when an object (e.g. a dirt collection region of a surface cleaning apparatus) is positioned in port 110. Pump 430 may be configured to direct fluid from reservoir 420 to nozzles 410 in response to actuator 402 determining an object is positioned in port 110. Alternatively, pump 430 may be configured to direct fluid to nozzles 410 after a pre-determined delay period following the detection of an object by sensor 402.

In the configuration exemplified in FIGS. 18 and 19, the dust control system includes one or more nozzles for dispersing water or other liquids into the air in the form of a mist or other dispersion. Alternatively, or additionally, the dust control system may include one or more ion emitters for selectively dispersing negative (and/or positive) ions in to the air. In operation, contacting the particulate matter with liquid will increase the weight of the particulate matter, including some or all of the finer particulate matter. This will increase the weight of the particulate matter and thereby reduce the likelihood of a plume or cloud forming. Similarly, particulate matter may become charged upon passage through a surface cleaning apparatus, e.g., a cyclone chamber. Exposing the particulate matter with oppositely charged ions will decrease the charge state of the particulate matter, including some or all of the finer particulate matter. This will reduce the tendency of the charged particulate matter to disperse and thereby reduce the likelihood of a plume or cloud forming.

Figure 20:
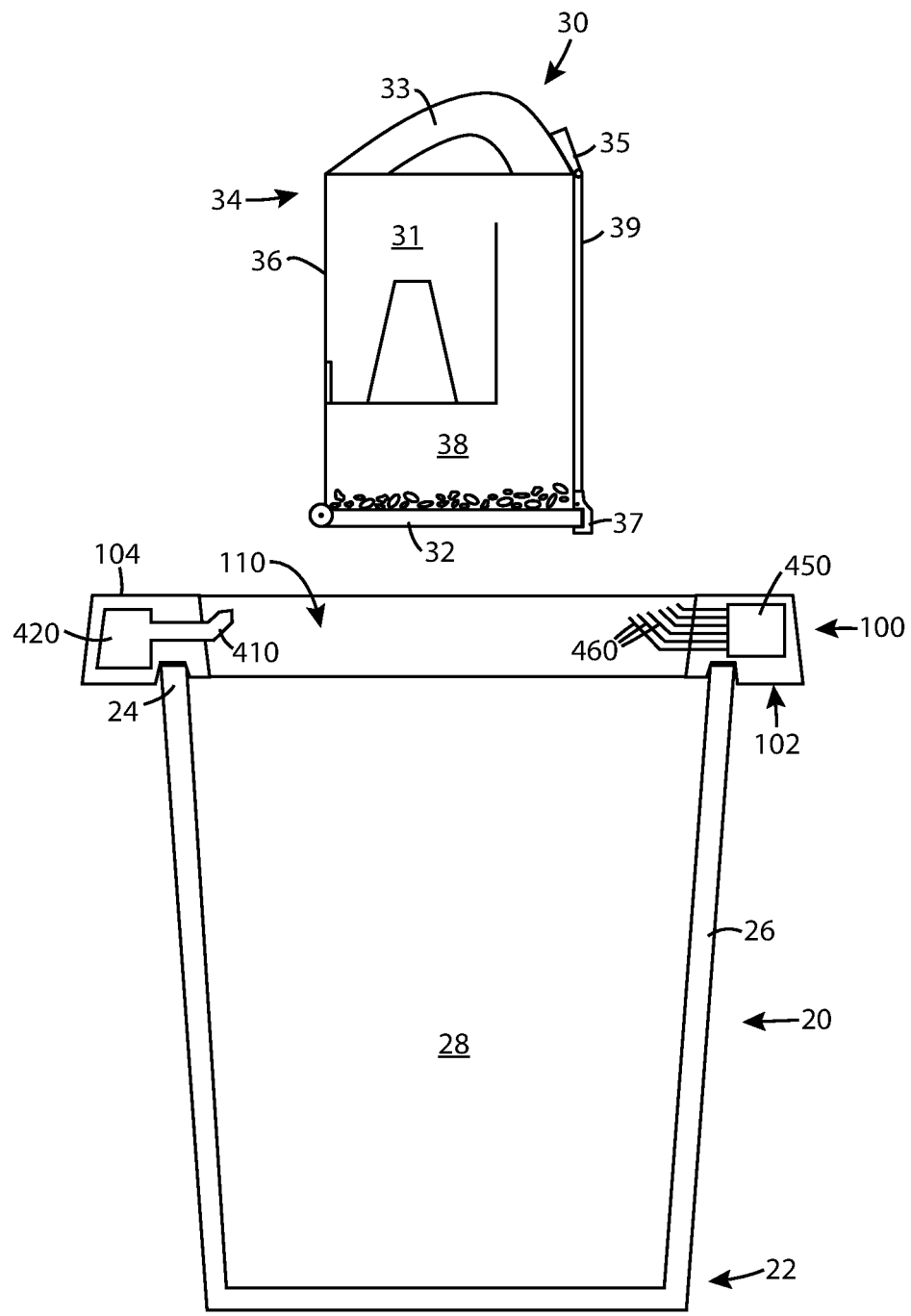
FIG. 20 is a cross section view of a container and first lid having an open port according to another embodiment, with the lid having first and second dust control members for providing dust control agents, with a cyclone dirt bin positioned above the container, the cyclone dirt bin being in a closed configuration.
Figure 21:
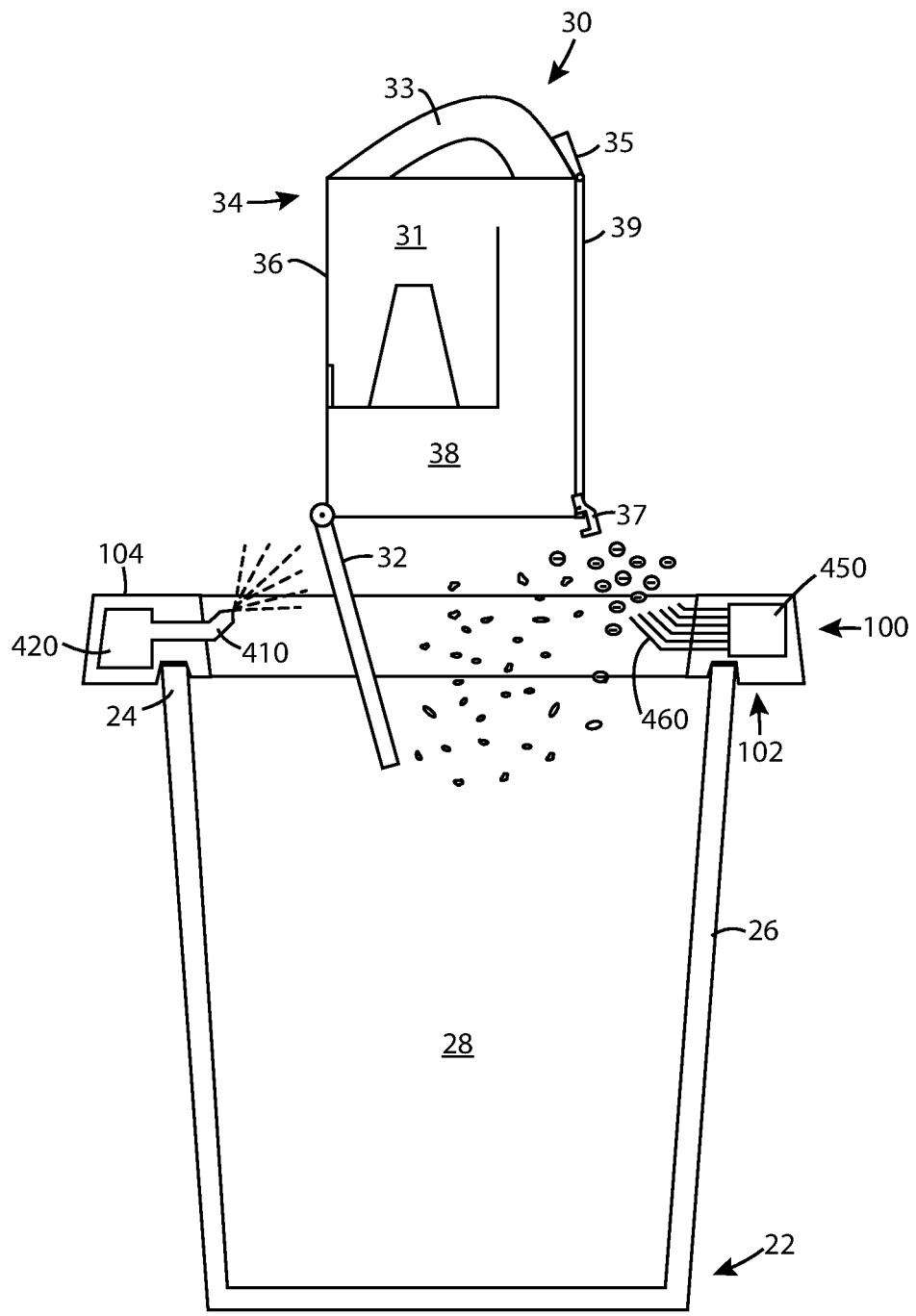
FIG. 21 is a cross section view of the container and first lid of FIG. 20, with the cyclone dirt bin in an open configuration, and with the first and second dust control members providing dust control agents.

In the configuration exemplified in FIGS. 20 and 21, the dust control system also includes a plurality of ion emitters 460 for imparting a negative (and/or positive) charge. Emitters 460 are provided on, e.g., an inner surface of port 110 between the upper surface 104 and a lower surface 102 of lid 100. As illustrated in FIG. 20, the emitters 460 are coupled to a, e.g., power source and control electronics 450 for providing the voltage to impart the charge.

In the illustrated example, emitters 460 are provided on an inner surface of port 110. Alternatively, or additionally, emitters 460 may be provided on the upper surface 104 of lid 100, or on the lower surface 102, or on container 20 itself.

Also, in the illustrated example a group of six emitters 460 is provided. It will be appreciated that more or fewer groups of more or fewer emitters 460 may be provided in alternative embodiments.

The operation of the dust control system in controlling dust, allergens, and other particulate matter when emptying a dirt collection region of a surface cleaning apparatus will now be discussed with reference to FIGS. 20 and 21.

In FIG. 20, a cyclone bin assembly 30 for a surface cleaning apparatus has been positioned above port 110. For example, a user may have detached and carried such a dirt collection region to such a position. Cyclone bin assembly 30 includes a dirt collection region 38 for collecting particulate matter dis-entrained from a dirty airflow by an air treatment member, in this case a cyclone 31.

In FIG. 21, openable lower end 32 of cyclone bin assembly 30 has been moved into an open position. For example, a user may have opened the dirt collection region, with the expectation that gravity would transfer at least the bulk of the contents of the dirt collection region to the interior of the refuse container. For example, door release switch 35 may have been deflected or rotated (e.g. by a user's thumb), resulting in a deflection or rotation of door closure member 37, whereby openable lower end 32 was released and moved to an open position, e.g. due to gravity or one or more biasing members (not shown).

As discussed previously, opening the dirt collection region 38 for emptying often results in a cloud or plume of fine dust or other particles billowing outwards from the opening of the dirt collection region and/or from the container 20 into which the dirt collection region is being emptied. The particles in such a plume or cloud may be dispersed during the emptying process, resulting in a less than complete transfer from the dirt collection region 38 to the interior 28 of the refuse container 20. This may be considered undesirable by a user, particularly if the plume or cloud contains dust or other allergens to which the user is sensitive.

To address this potential issue, in FIG. 21 pump 430 has been actuated to direct a liquid, e.g., water, to nozzles 410, resulting in a spray or mist of water particles being dispersed in the region above port 110 (i.e. the area or region below the outlet of the dirt collection region 38 in the illustrated example). Advantageously, this may result in some or all of any particles dispersed in a plume or cloud following the opening of dirt collection region 38 being 'wetted' by the dispersed water droplets, and thereafter drawn into the interior volume 28 of container 20 by gravity.

Also, in FIG. 21 control electronics 450 have been actuated to cause ion emitters 460 to emit, e.g., negatively charged particles, resulting in a negative ions being dispersed in the region above port 110. Advantageously, this may result in some or all of the charged particulate matter being neutralized. This results in the particulate matter having a lesser tendency to disperse following the opening of dirt collection region 38 and thereby a lower likelihood of a plume being formed or a smaller plume being formed.

Accordingly, the amount of dust, allergens, or other fine particulate matter that is 'lost' (i.e. is not transferred to container 20) during the emptying of dirt collection region 38 into container 20 may be reduced or eliminated.

In the examples illustrated in FIGS. 18-21, a dust control system is provided in association with a refuse container and/or with a lid for a refuse container. Alternatively, or in addition, a dust control system may be provided in association with a surface cleaning apparatus, or a portion thereof such as an air treatment member (which may be characterized as a dirt separation member) and/or a dirt collection region. Accordingly, the dust control system may be configured to selectively direct a dust control agent towards the interior volume of the dirt collection region and/or a region below the openable portion of a dirt collection region.

Figure 22:
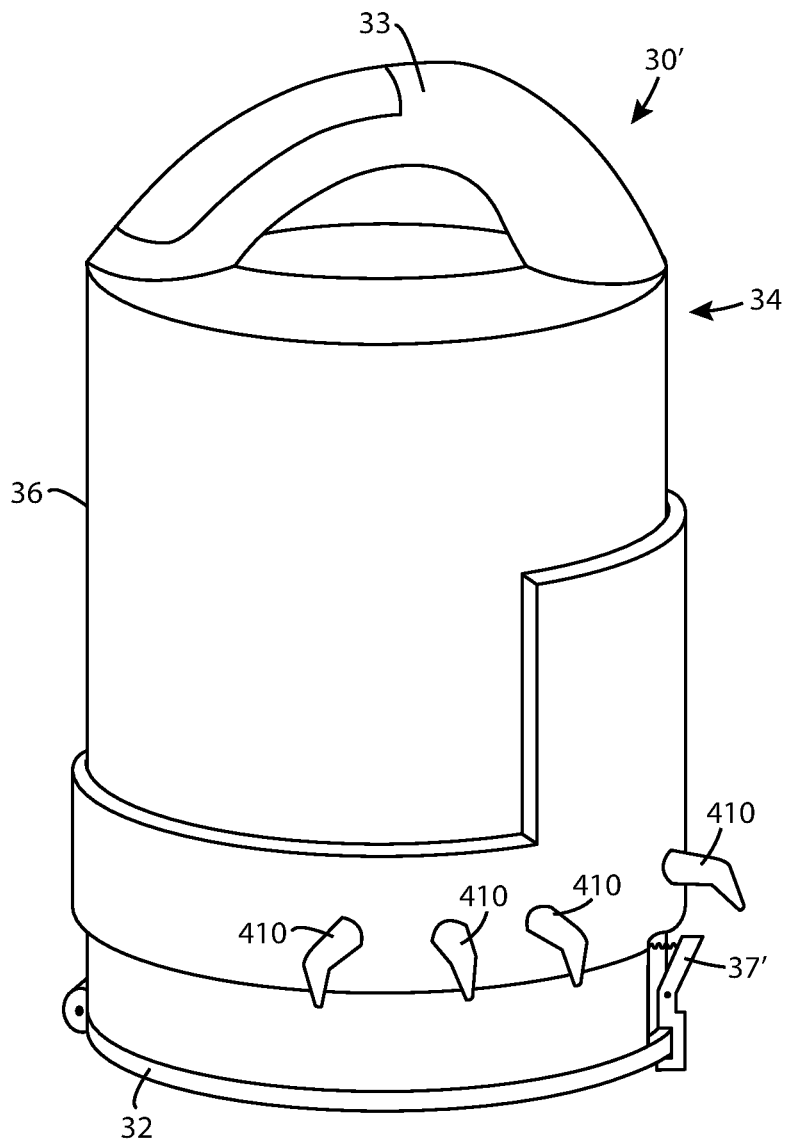
FIG. 22 is a perspective view of a cyclone bin assembly having a dust control member for providing a dust control agent according to one embodiment.
Figure 23:
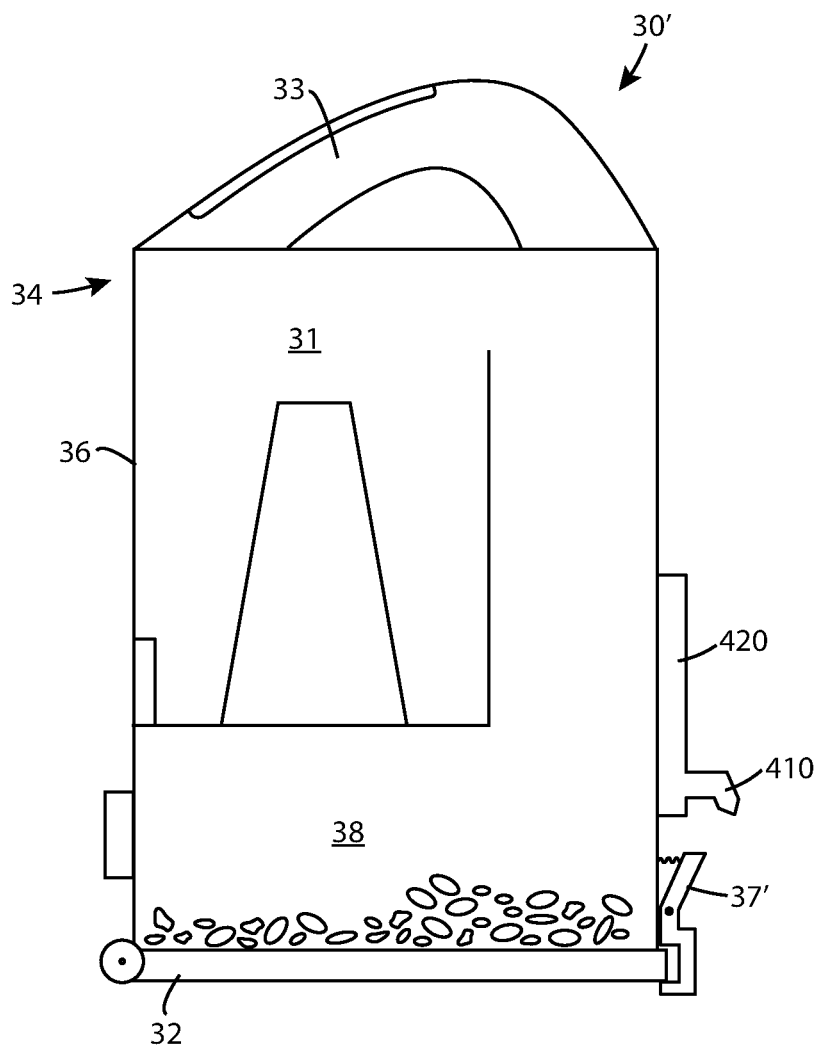
FIG. 23 is a cross section view of a cyclone bin assembly having a dust control member for providing a dust control agent according to another embodiment, the cyclone dirt bin being in a closed configuration.
Figure 24:
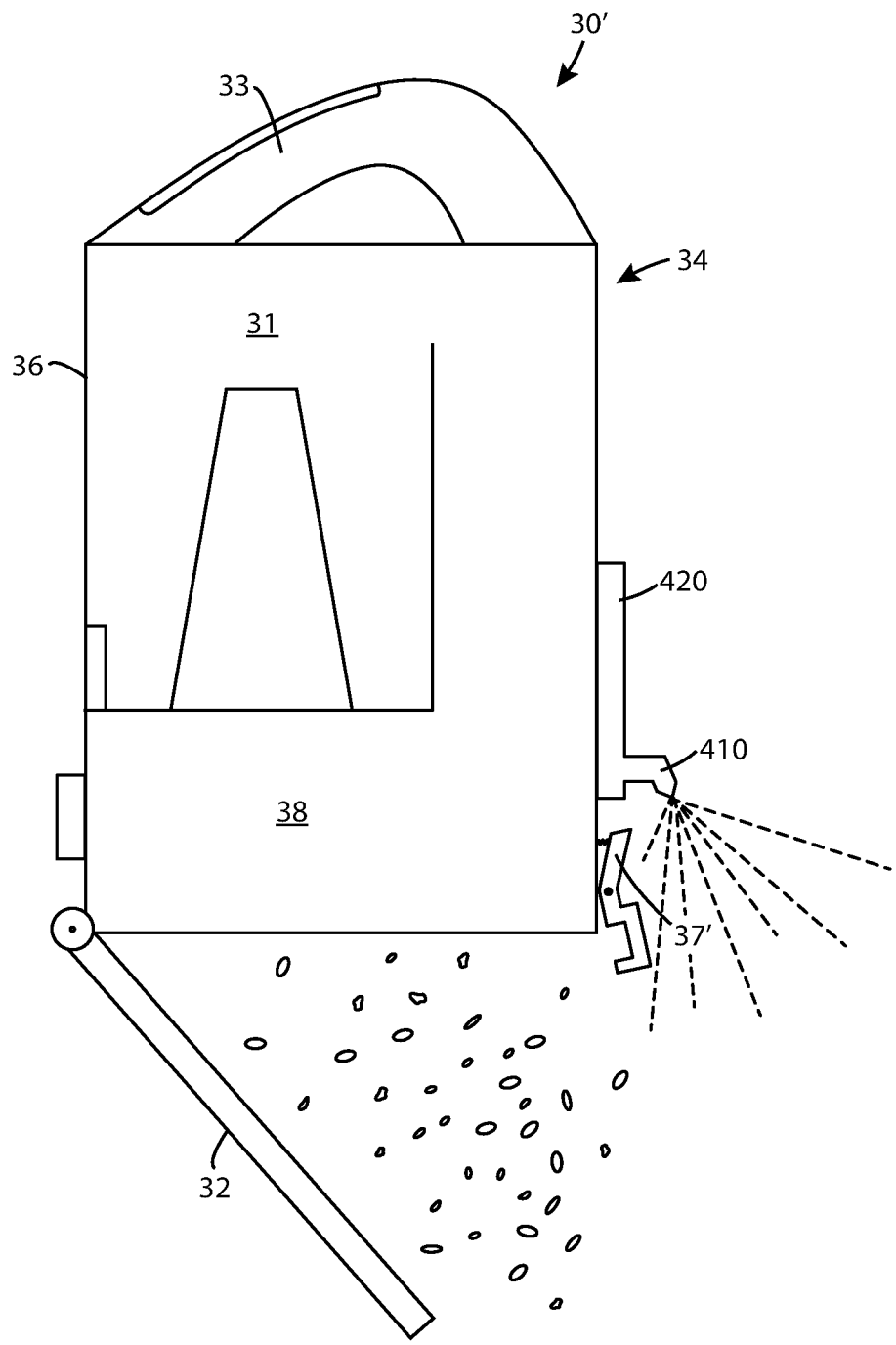
FIG. 24 is a cross section view of the cyclone bin assembly of FIG. 23, with the cyclone dirt bin in an open configuration, and with the dust control member providing a dust control agent.

As exemplified in FIGS. 22-24, the dust control system includes a plurality of nozzles 410 for dispersing a liquid, e.g. water, into the air in the form of a mist or other dispersion. Nozzles 410 are provided on an outer surface of sidewall 36 between the upper end 34 and lower end 32 of bin assembly 30. As illustrated in FIG. 23, the nozzles 410 are in fluid communication with a reservoir 420. Reservoir 420 is configured to store a liquid to be dispersed (e.g. water).

In the illustrated example, four nozzles 410 are shown. Alternatively, five or more nozzles 410 may be provided, or three or two or only one nozzle 410 may be provided.

The operation of the dust control system in controlling dust, allergens, and other particulate matter when emptying a dirt collection region of a surface cleaning apparatus will now be discussed with reference to FIGS. 23 and 24.

In FIG. 23, openable end or door 32 for dirt collection region 38 is in a closed position, and particulate matter dis-entrained from a dirty airflow by an air treatment member, in this case a cyclone 31, has been collected in the dirt collection region 38.

In FIG. 24, openable lower end 32 has been moved into an open position. For example, a user may have opened the dirt collection region, with the expectation that gravity would transfer at least the bulk of the contents of the dirt collection region to e.g. the interior of a refuse container. For example, door closure member 37' may have been deflected or rotated (e.g. by a user's thumb), whereby openable lower end 32 was released and moved to an open position, e.g. due to gravity or one or more biasing members (not shown).

Also, in FIG. 24 a pump has been actuated to direct liquid, e.g., water, to nozzles 410, resulting in a spray or mist of water particles being dispersed in the region around the opening of dirt collection region 38. As discussed previously, opening the dirt collection region 38 for emptying often results in a cloud or plume of fine dust or other particles billowing outwards from the opening of the dirt collection region. Advantageously, the dispersal of water particles in the region around the opening of dirt collection region 38 may result in some or all of any particles dispersed in a plume or cloud following the opening of dirt collection region 38 being 'wetted' by the dispersed water droplets, and thereafter drawn into e.g. the interior volume 28 of a refuse container by gravity.

Accordingly, the amount of dust, allergens, or other fine particulate matter that is dispersed into the air during the emptying of dirt collection region 38 may be reduced or eliminated.

The dust control system provided with a cyclone bin assembly may be actuated in a number of ways and may be actuated using any method of actuation discussed herein. For example, a manual dust control system actuator, e.g. a depressible button, may be provided. Fluid pump may be configured to direct fluid from reservoir 420 to nozzles 410 in response to such an actuator being depressed. Alternatively, it may be actuated by the opening of the dirt collection region.

Figure 25:
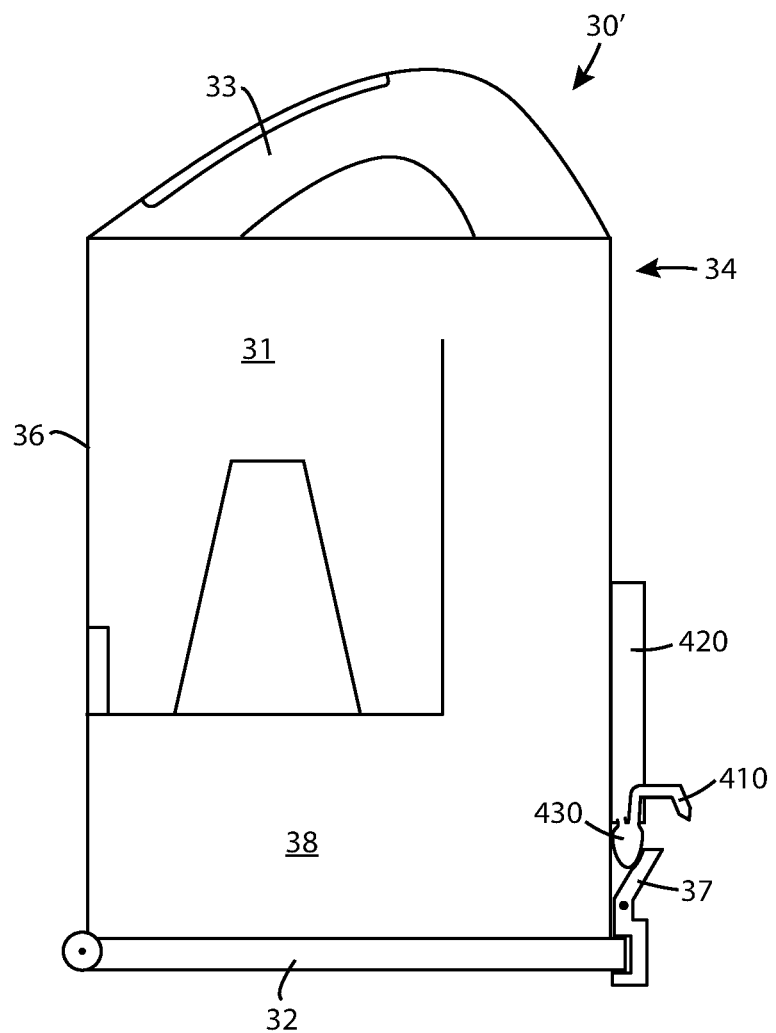
FIG. 25 is a cross section view of a cyclone bin assembly having a dust control member for providing a dust control agent according to another embodiment, the dust control member being configured to automatically provide a dust control agent when an openable door of a dirt collection region is opened.

For example, in the configuration illustrated in FIG. 25, at least a portion of bellows-type pump 430 is positioned between door closure member 37' and sidewall 36 of the cyclone bin assembly. In this arrangement, pump 430 may be actuated substantially concurrently with the deflection or rotation of door closure member 37' (e.g. by a user's thumb), whereby a spray or mist of water particles being dispersed from nozzles 410 substantially concurrently with the opening of openable lower end 32. In other words, in such an arrangement pump 430 is configured to direct fluid from reservoir 420 to nozzles 410 in response to door closure member 37' being actuated.

Figure 26:
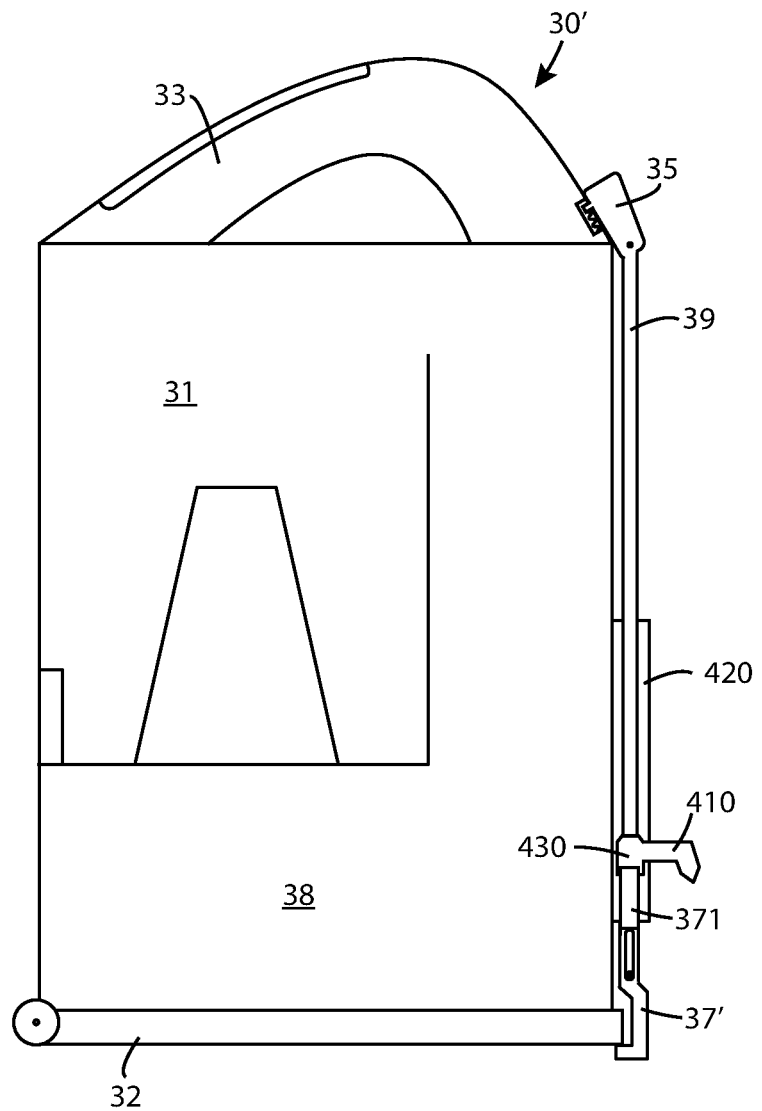
FIG. 26 is a cross section view of a cyclone bin assembly having a dust control member for providing a dust control agent according to another embodiment, the dust control member being configured to automatically provide a dust control agent and subsequently open an openable door of a dirt collection region.

Alternatively, in the configuration illustrated in FIG. 26, a door release switch 35 provided adjacent handle 33 is operatively coupled to door closure member 37 via door actuator 39. In this example, a piston-type pump 430 is provided at the base of door actuator 39, such that downward travel of door actuator 39 results in a spray or mist of water particles being dispersed from nozzles 410. Also, a secondary door actuator 371 is provided at the base of the cylinder of the piston-type pump 430. In this configuration, further downward travel of door actuator 39—i.e. after pump 430 has been actuated—results in contact and downward travel of secondary door actuator 371, thereby resulting in a deflection of door closure member 37, whereby openable lower end 32 is released. In other words, in such an arrangement pump 430 is configured to direct fluid from reservoir 420 to nozzles 410 prior to door closure member 37' being actuated. Or, put another way, in such an arrangement openable lower end 32 is configured to automatically open after a spray or mist of water particles has been dispersed from nozzles 410.

Figure 27:
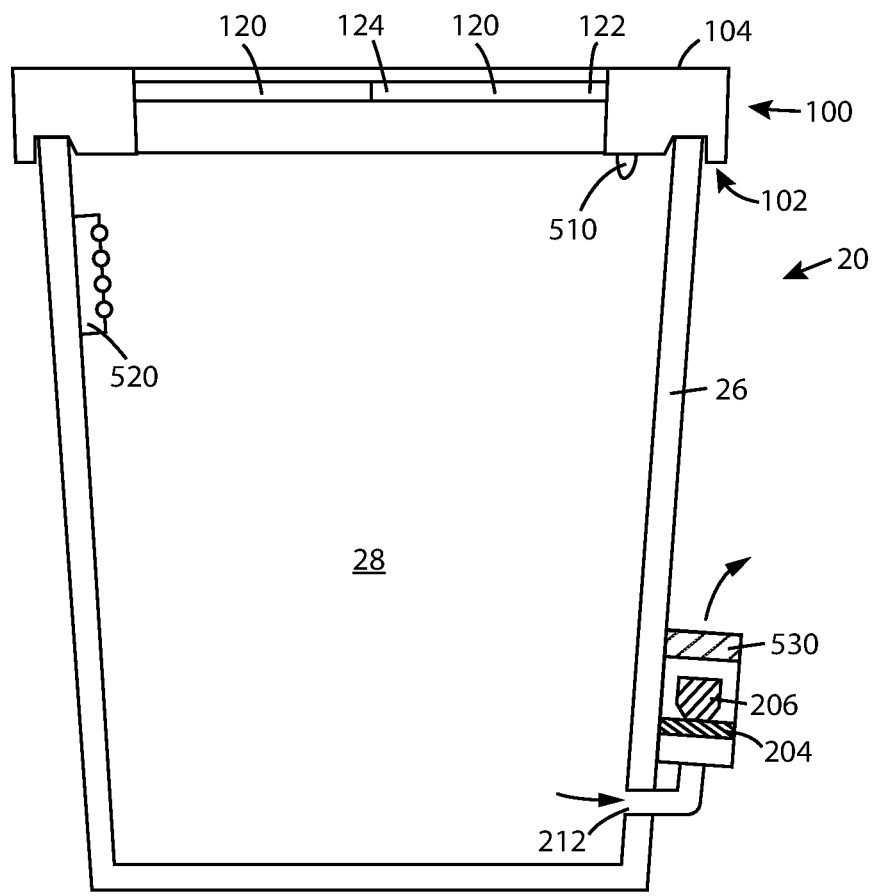
FIG. 27 is a cross section view of a container, a lid, and a suction source according to another embodiment, with an ozone gas emitter provided on an interior wall of the container, and with a UV light source provided on the lid.
Figure 28:
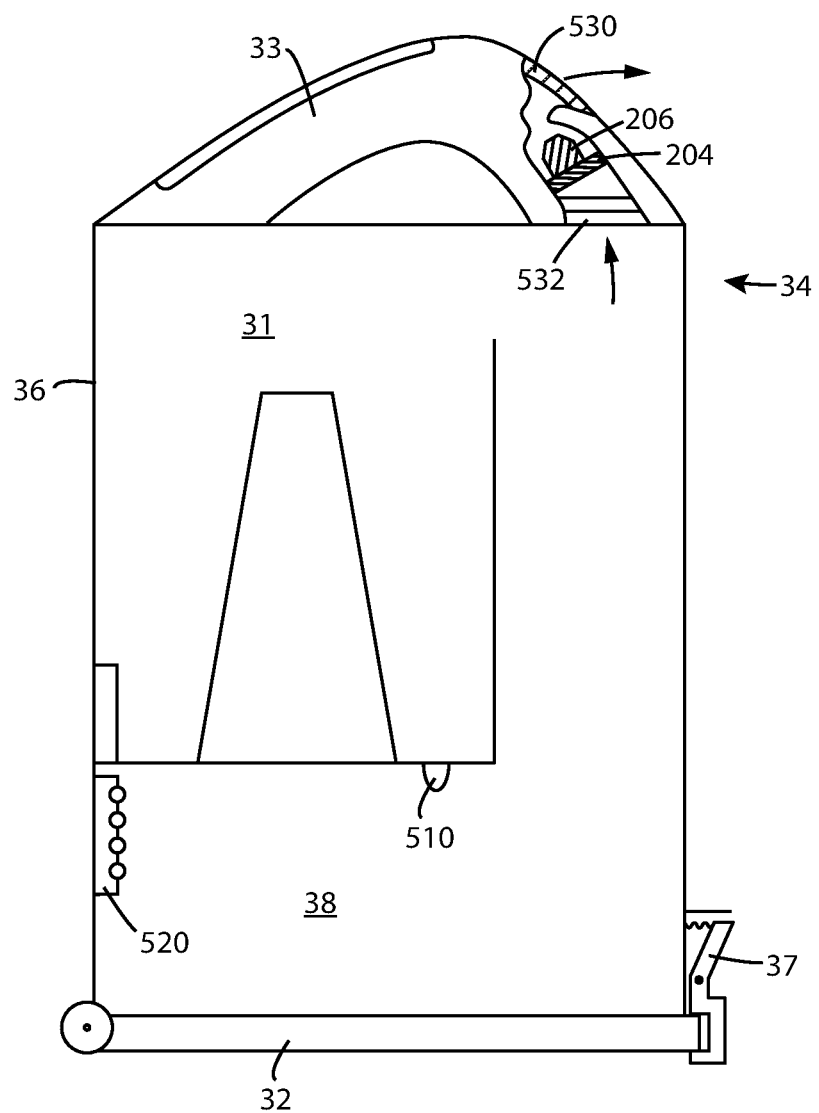
FIG. 28 is a cross section view of cyclone bin assembly according to another embodiment, with a UV light source and an ozone gas emitter provided in the dirt collection region, and with a suction source and ozone destructor material.

FIGS. 27 and 28 exemplify the use of a dust treatment agent.

As exemplified in FIG. 27, the dust treatment system includes a UV light emitter 510 that selectively emits UV light into interior volume 28 of container 20, and an ozone gas emitter 520 that selectively emits ozone gas into interior volume 28 of container 20. It will be appreciated that only one treatment member may be used.

In some embodiments, a manual actuator (e.g. a depressible button) may be provided to selectively actuate the dust treatment system to provide one or more treatment agents (e.g. UV light, ozone gas) into interior volume 28 of container 20. For example, the UV light emitter 510 may be configured such that, in response to depression of the manual actuator, it emits UV light for a pre-set period of time (e.g. 90 seconds). Similarly, the ozone gas emitter 520 may be configured such that, in response to depression of the manual actuator, it emits ozone gas for a pre-set period of time (e.g. 90 seconds). Alternatively, or additionally, the dust treatment system may be configured such that one or more treatment agents (e.g. UV light, ozone gas) are provided into interior volume 28 of container 20 at pre-set intervals (e.g. every 24 hours) without requiring manual actuation, and/or upon emptying a dirt collection region and/or a preset time after a dirt collection region is emptied into the refuse container.

Ozone gas may be effective for purifying and/or deodorizing refuse collected in container 20. However, ozone gas may be also harmful if inhaled by humans or other animals. In an effort to minimize one or more risks associated with emitting ozone gas, some embodiments that include an ozone gas emitter 520 may also include an ozone destructor material for breaking down some or all of the emitted ozone.

For example, as illustrated in FIG. 27, a suction source 220 that includes a suction motor 206 drivingly connected to a suction fan 204 may be provided for drawing air (including emitted ozone) from the interior volume 28 of container 20 via an inlet 212 and across an ozone destructor material 530. The ozone destructor material 530 may be any material that can remove ozone gas from the air flow by adsorption or conversion to one or more other molecules. Examples include activated carbon or an ozone catalyst that converts ozone ($O_3$) to oxygen ($O_2$). An advantage of this design is that some or all of the ozone gas emitted into interior volume 28 to counteract organisms in container 20 may be removed before the air flow is discharged from container 20. This may allow a container 20 including ozone gas emitter 520 to be safely employed in, e.g. residential spaces.

In the example illustrated in FIG. 27, a dust treatment system is provided in association with a refuse container and/or with a lid for a refuse container. Alternatively, a dust treatment system may be provided in association with an air treatment member such as a cyclone bin assembly. As exemplified in FIG. 28, a cyclone bin assembly 30 for a surface cleaning apparatus has a dust treatment system for selectively introducing a dust treatment agent into a dirt collection region of a surface treatment apparatus. By providing one or more disinfecting agents, e.g. ultra-violet (UV) light, ozone ($O_3$), and hydrogen peroxide ($H_2O_2$), into a dirt collection region, growth of undesirable organisms present in dust, dirt, and/or other refuse collected in the dirt collection region may be reduced or eliminated.

In the configuration illustrated in FIG. 28, the dust treatment system includes a UV light emitter 510 that emits UV light into dirt collection region 38 of cyclone bin assembly 30, and an ozone gas emitter 520 that selectively emits ozone gas into dirt collection region 38. It will be appreciated that only one treatment member may be used.

In some embodiments, a manual actuator (e.g. a depressible button) may be provided to selectively actuate the dust treatment system to provide one or more treatment agents (e.g. UV light, ozone gas) into dirt collection region 38 of cyclone bin assembly 30. For example, the UV light emitter 510 may be configured such that, in response to depression of the manual actuator, it emits UV light for a pre-set period of time (e.g. 90 seconds). Similarly, the ozone gas emitter 520 may be configured such that, in response to depression of the manual actuator, it emits ozone gas for a pre-set period of time (e.g. 90 seconds). Alternatively, or additionally, the dust treatment system may be configured such that one or more treatment agents are provided into interior volume 28 of container 20 at pre-set intervals (e.g. every 24 hours) without requiring manual actuation. Alternatively, or additionally, the dust treatment system may be configured such that one or more treatment agents are provided into interior volume 28 of container 20 after a pre-set number of uses of the surface cleaning apparatus (e.g. following 5 on/off cycles of the main suction motor of the surface cleaning apparatus). Alternatively, or additionally, the dust treatment system may be configured such that one or more treatment agents are provided into interior volume 28 of container 20 subsequent to emptying of the dirt collection region (e.g. in response openable door 32 being closed).

In an effort to minimize one or more risks associated with emitting ozone gas, the example illustrated in FIG. 28 includes a suction source 220 that includes a suction motor 206 drivingly connected to a suction fan 204 for drawing air (including emitted ozone) from dirt collection region 38 via an inlet 532 and across an ozone destructor material 530. As discussed above, ozone destructor material 530 may be any material that can remove ozone gas from the air flow by adsorption or conversion to one or more other molecules. Examples include activated carbon or an ozone catalyst that converts ozone ($O_3$) to oxygen ($O_2$). An advantage of this design is that some or all of the ozone gas emitted into dirt collection region 38 of cyclone bin assembly 30 may be drawn across an ozone destructor material before being otherwise exhausted into the ambient atmosphere (e.g. by opening openable door 32). This may allow a cyclone bin assembly 30 including ozone gas emitter 520 to be safely employed in, e.g. residential spaces.

Sub-Atmospheric Pressure Mode for Dirt Collection Region of a Surface Treatment Apparatus The following is a general description of a dirt collection region of a surface treatment apparatus having a sub-atmospheric pressure mode and other features set out herein that may be used by itself or in combination with one or more embodiments disclosed herein, including one or more of a lid for a refuse container having an openable port, a refuse container having a suction source, a cyclone bin assembly having a deployable closure member, dust control systems for refuse containers or surface treatment apparatus, and dust treatment systems for refuse containers or surface treatment apparatus. The following description contains various features of a dirt collection region of a surface treatment apparatus having a sub-atmospheric pressure mode that may be used individually or in any combination or sub-combination.

In accordance with this aspect, sub atmospheric pressure is provided in an air treatment member or a portion thereof, e.g., a dirt collection region, to draw finer particulate matter into the surface cleaning apparatus. An advantage of this aspect is that a reduced amount of finer particulate matter may be released when the dirt collection region is opened and therefore a smaller plume may be formed upon emptying the dirt collection region.

It will be appreciated that the sub atmospheric pressure may be produced by the suction motor (which may be referred to as a main suction motor) used to draw air from a dirty air inlet when a surface cleaning apparatus is used to clean a surface (i.e., a cleaning mode). In such a case, the main suction motor may be operated at a lower power level to produce a reduced level of suction during an emptying operation (i.e., an emptying mode). For example, the main suction motor may be configured to produce sufficient suction to create an air flow of 0.1 CFM to 1.5 CFM per square inch of opening area during the emptying mode, preferably 0.25 CFM to 1.25 CFM per square inch of opening during the emptying mode and more preferably 0.50 CFM to 1.00 CFM per square inch of opening area during the emptying mode. Alternatively, or in addition, dilution air may be drawn from outside the air treatment member, such as by opening a vent hole, between the main suction motor and the air treatment member during the emptying mode. An advantage of this latter approach is that the suction motor may be operated at the same power level during both cleaning and emptying.

Alternatively, or in addition, the sub atmospheric pressure may be produced during the emptying mode by an alternate suction motor for use during a cleaning cyclone, i.e., an emptying mode suction motor. An advantage of this design is that a smaller, and therefore lighter, suction motor and fan assembly may be used. Such a suction motor may be removable with the dirt collection region (e.g., part of a removable cyclone bin assembly or dirt collection region), thereby permitting a removable dirt collection to be used in conjunction with this aspect.

It will be appreciated that the suction motor, whichever is used, may be actuated prior to, upon, or subsequent to opening the dirt collection region for emptying. For example, one or more sensors configured to detect when an openable door of the dirt collection region is opened may be provided to automatically actuate whichever suction motor is to be used during the emptying mode in response to the openable door being opened.

It will also be appreciated that the air which is drawn from the air treatment member during an emptying operation (i.e., the emptying mode) may also be treated to remove particulate matter. Any air treatment member may be used. For example, the air may be drawn through a cyclone and/or an alternate or emptying mode pre-motor filter.

As exemplified in FIGS. 29-32, a cyclone bin assembly (a main air treatment member) is shown schematically coupled to a suction system of surface cleaning apparatus. In the illustrated schematics, cyclone bin assembly 30 includes a cyclone 31, and a dirt collection region 38 in communication with cyclone 31 via cyclone dirt outlet 633 for collecting particulate matter dis-entrained from a dirty airflow by cyclone 31. Cyclone bin assembly 30 has an openable lower end 32 releasably secured by a door closure member 37'. It will be appreciated that any air treatment member may be used as the main air treatment member.

Figure 29:
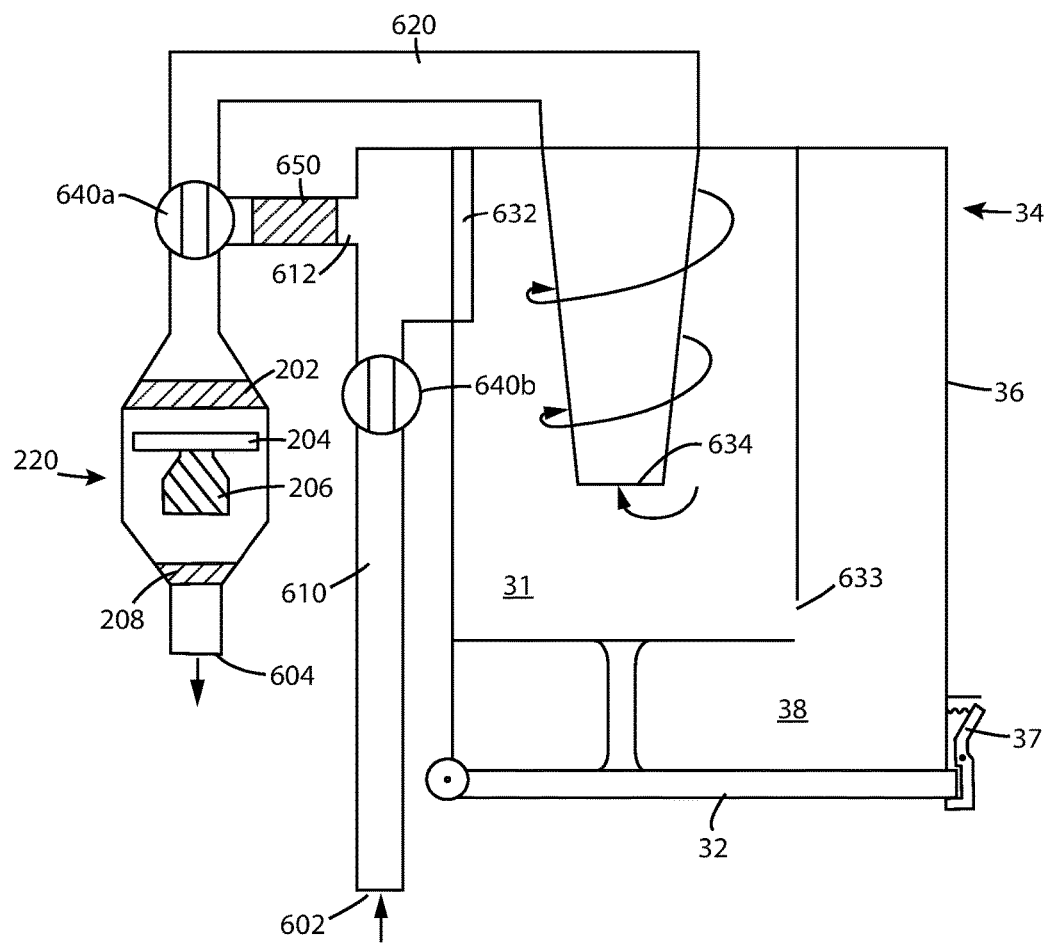
FIG. 29 is a schematic cross-section view of a cyclone bin assembly according to another embodiment, with conduit and a valve to direct suction from a suction source for selectively drawing air out of the cyclone bin assembly via the cyclone dirty air inlet or via the cyclone air outlet, with an openable door of a dirt collection region being in a closed configuration, and with the suction source drawing air out of the cyclone bin assembly via the cyclone air outlet.

Referring to FIG. 29, in operation dirty air (e.g. an airflow with entrained particulate matter) enters a dirty air inlet 602 of the surface cleaning apparatus and is drawn through a conduit 610 to a cyclone dirty air inlet 632. After circulating in cyclone 31, and thereby dis-entraining particles contained therein, the air passes through cyclone air outlet 634 and is drawn through a conduit 620 by a suction fan 204 drivingly connected to a main suction motor 206 and exhausted from a clean air outlet 604 of the surface cleaning apparatus. In the illustrated example, an optional main or first pre-motor filter 202 and an optional main or first post-motor filter 208 are also shown upstream and downstream, respectively, of suction motor 206, although it will be appreciated that one or both of these filters may not be provided in alternative embodiments. Any known surface cleaning apparatus with any known cyclone assembly or other air treatment member may be used.

As discussed previously, opening the dirt collection region 38 for emptying often results in a cloud or plume of fine dust or other particles billowing outwards from the opening of the dirt collection region. The particles in such a plume or cloud may be dispersed during the emptying process, resulting in a less than complete transfer from the dirt collection region 38 to e.g. a refuse container. This may be considered undesirable by a user, particularly if the plume or cloud contains dust or other allergens to which the user is sensitive.

Figure 30:
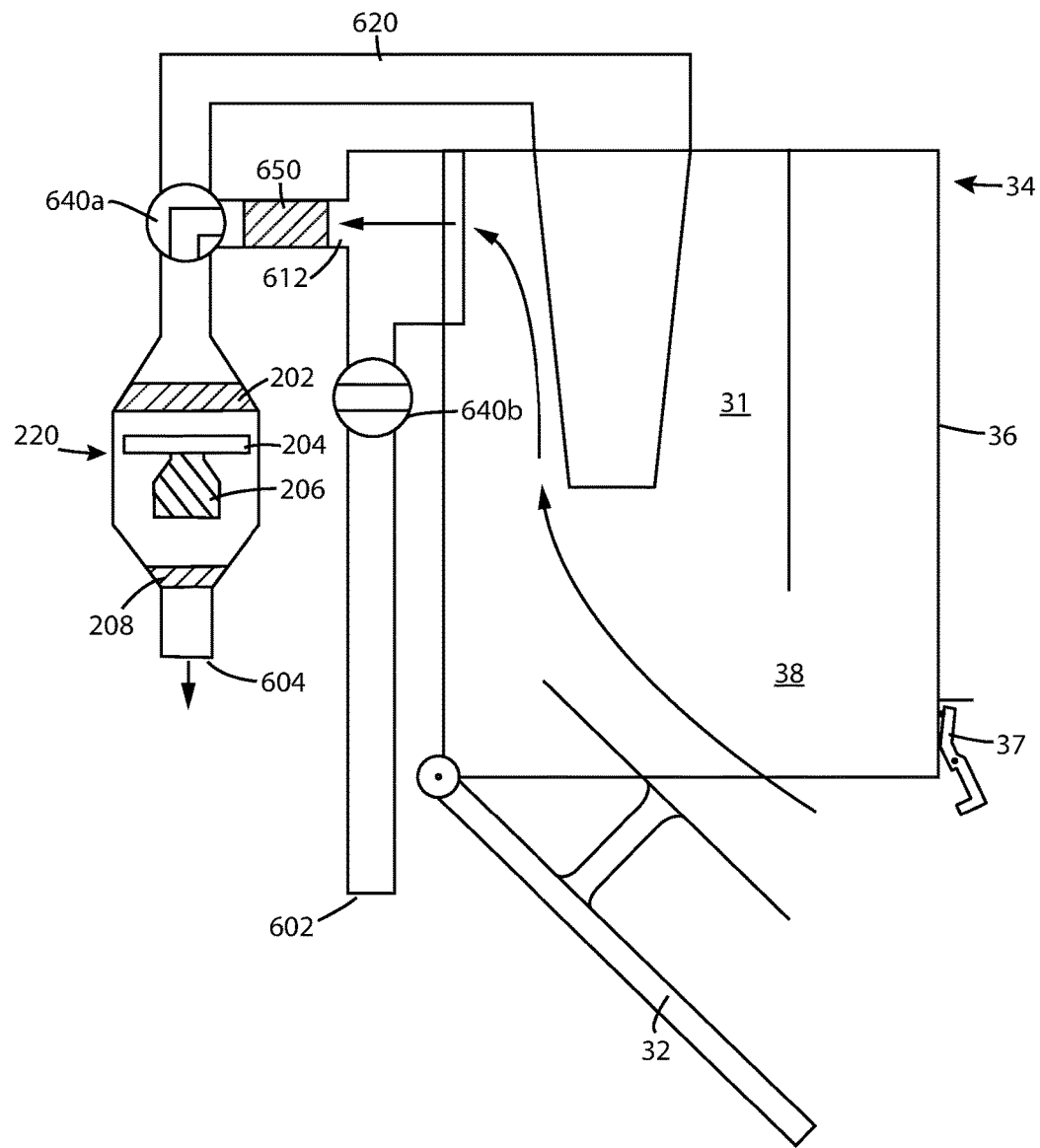
FIG. 30 is a schematic cross-section view of the cyclone bin assembly of FIG. 29, with the openable door in an open configuration, and with the suction source drawing air out of the cyclone bin assembly via the cyclone dirty air inlet.

As exemplified in FIGS. 29 and 30, the main suction motor used during a cleaning operation is used to create the sub atmospheric pressure during emptying of the dirt collection region (e.g. when the openable door is in an open position). The suction motor may be connected to draw air from the cyclone by any method and may use the cyclone air outlet. As exemplified, a bypass conduit 612, which functions as an alternate downstream air flow path, and valves 640a, 640b are provided. For example, in the configuration shown in FIG. 30, main suction fan 204 and main suction motor 206 are shown being used to draw air from cyclone air inlet 632 via conduit 612, resulting in an airflow from the dirt collection region 38 via cyclone dirt outlet 633 and cyclone 31, through conduit 612 and an optional auxiliary or emptying mode backflow pre-motor filter 650, and through post-motor filter 208 to an area exterior of the air treatment member. Advantageously, this may result in some or all of any particles that might otherwise be dispersed in a plume or cloud following the opening of dirt collection region 38 being drawn back into auxiliary backflow filter 650. Accordingly, the amount of dust, allergens, or other fine particulate matter that is 'lost' (e.g. is not transferred to a refuse container) during the emptying of dirt collection region 38 may be reduced or eliminated. In an alternate embodiment as exemplified in FIG. 32, it will be appreciated that the alternate downstream air flow path may extend from the main air treatment member (cyclone 31 as exemplified) to the main suction motor 206 and bypass the main pre-motor filter 202. In such a case, auxiliary backflow pre-motor filter 650 may be the only filter upstream of suction motor 206.

It will be appreciated that in some embodiments, suction motor 206 may be operated at reduced power when drawing air from cyclone air inlet 632. An advantage of such a configuration is that only very fine dust or other particles may be drawn towards auxiliary backflow filter 650, while larger particles may be relatively unaffected by the reduced airflow. For example, when openable lower end 32 of cyclone bin assembly 30 has been moved into an open position, larger dirt particles collected in the dirt collection region may be directed by gravity to the interior of a refuse container over which the cyclone bin assembly 30 is positioned.

In the examples illustrated in FIGS. 29 and 30, the same suction source used during normal operation of the surface cleaning apparatus is used to drawing air from cyclone air inlet 632 during emptying of the dirt collection region 38. Alternatively, an auxiliary or emptying mode suction source may be provided to draw air from the cyclone, such as from cyclone air inlet 632.

Figure 31:
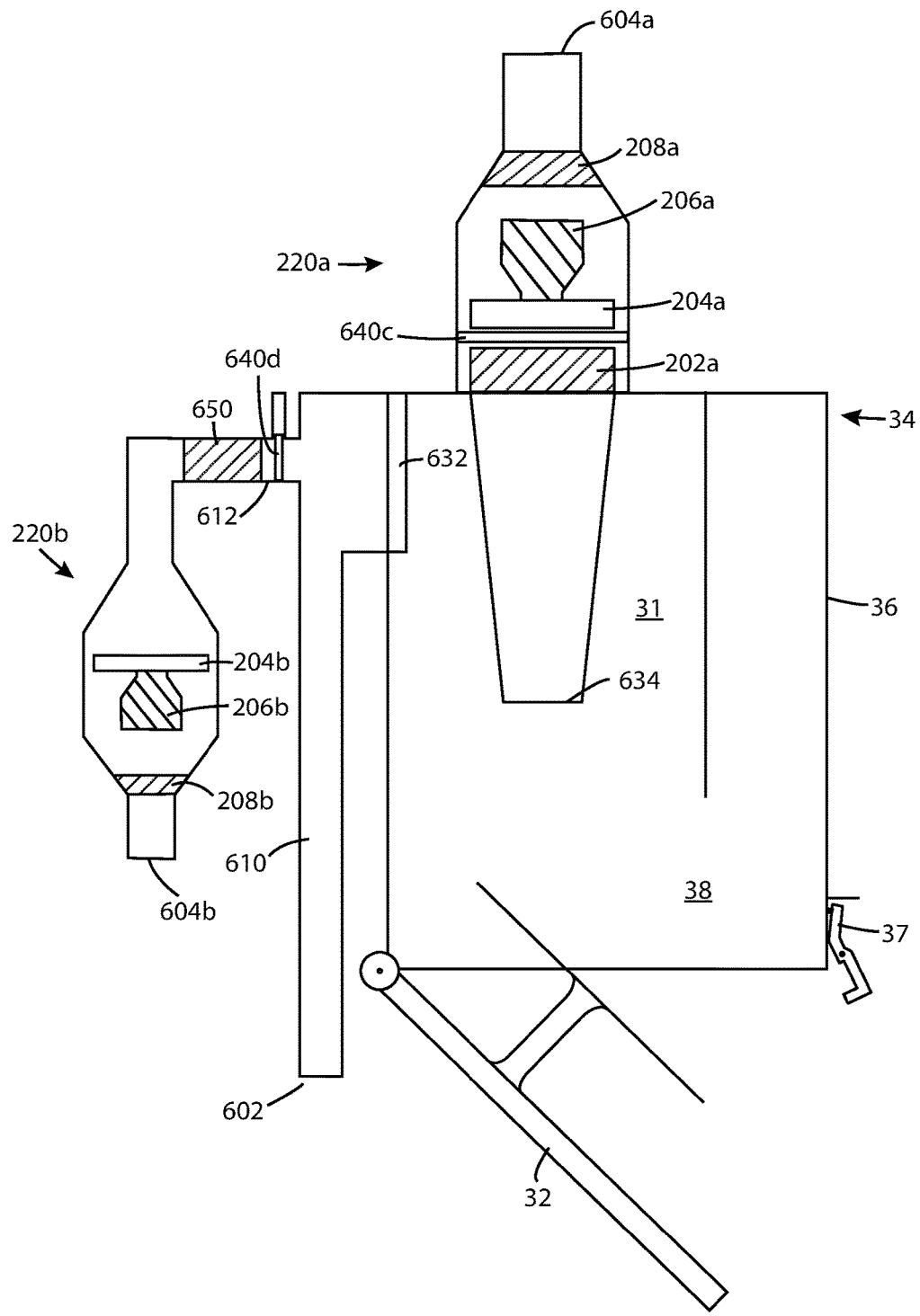
FIG. 31 is a schematic cross-section view of a cyclone bin assembly according to another embodiment, with an auxiliary suction source for drawing air out of the cyclone bin assembly via the cyclone dirty air inlet, with an openable door of a dirt collection region being in a closed configuration, and with the suction source drawing air out of the cyclone bin assembly via the cyclone air outlet.

For example, as illustrated in FIG. 31, a main suction source 220a, which may be referred to as a main suction motor or a main suction motor and fan assembly, may be provided downstream of cyclone air outlet 634 for drawing air through cyclone 31 during normal operation of the surface cleaning apparatus (the cleaning mode). For example, suction fan 204a may be used to induce an airflow from dirty air inlet 602 through cyclone air inlet 632, around cyclone 31, through cyclone air outlet 634, and exiting from clean air outlet 604a of the surface cleaning apparatus.

During emptying of the dirt collection region (the emptying mode), emptying mode suction fan 204b and emptying mode suction motor 206b may be used to draw air from cyclone air inlet 632 via conduit 612, resulting in an airflow from the dirt collection region 38 via cyclone dirt outlet 633 and cyclone 31, through conduit 612 and optional auxiliary backflow filter 650, and through post-motor filter 208b to an auxiliary clean air outlet 604b. Advantageously, this may result in some or all of any particles dispersed in a plume or cloud following the opening of dirt collection region 38 being drawn back into auxiliary backflow filter 650.

It will be appreciated that the air flow path through which air travels during the emptying mode (the alternate downstream air flow path), whichever suction motor is used, may be closed during the cleaning mode and opened during an emptying mode. Similarly, the flow path from the main air treatment member to the main suction motor (a main downstream portion of the air flow path) is open during the cleaning mode and may be closed during the emptying mode. A main closure member may be associated with the main downstream portion of the air flow path and an alternate closure member may be associated with the alternate downstream air flow path. These closure members may be provided at the inlets to these air flow paths and may be any closure member such as a valve, a sliding closure panel, or the like.

Figure 32:
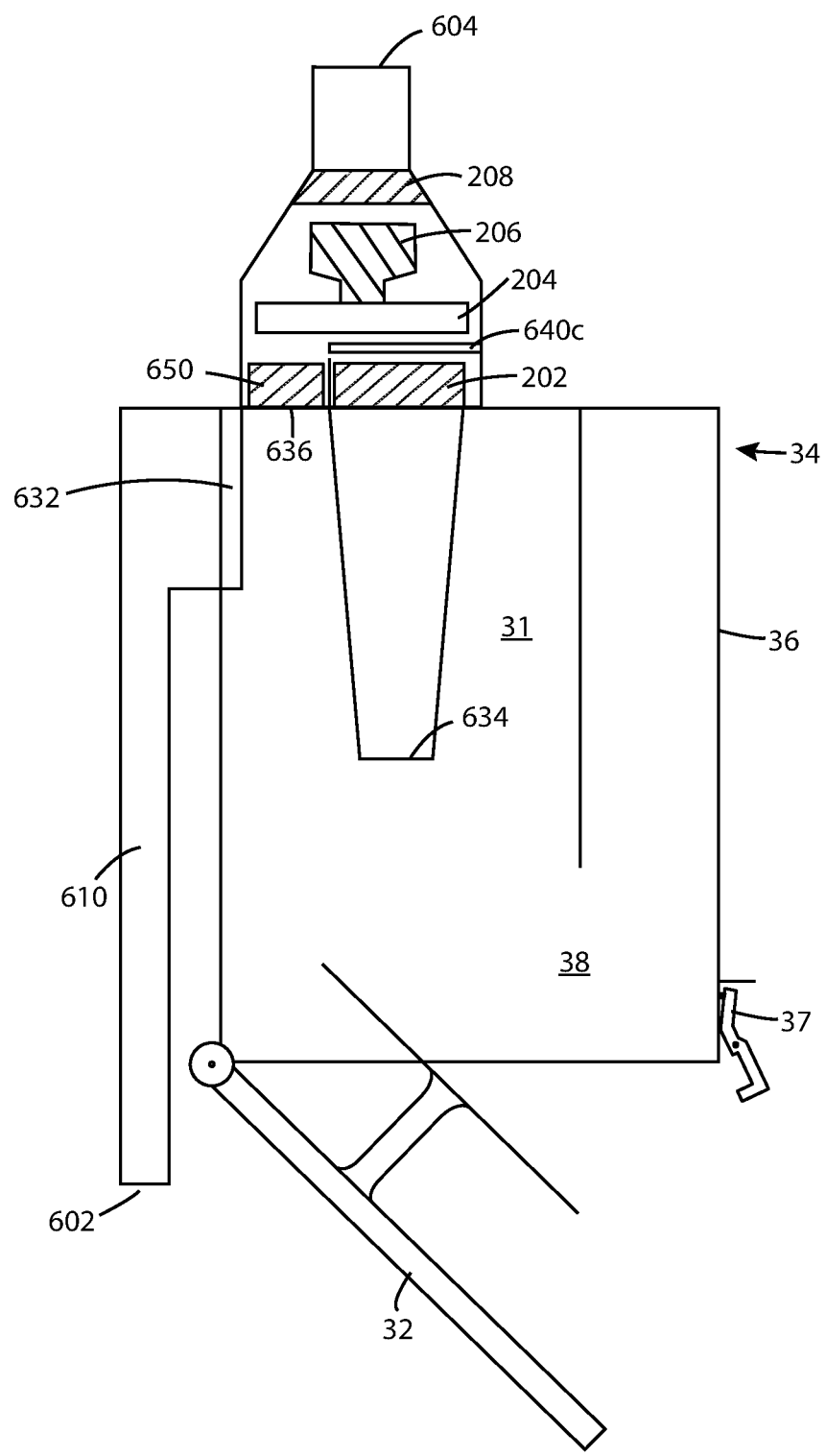
FIG. 32 is a schematic cross-section view of a cyclone bin assembly according to another embodiment, with a valve to direct suction from a suction source for selectively drawing air out of the cyclone bin assembly via the cyclone air outlet and an auxiliary cyclone air outlet proximate the cyclone dirty air inlet, with an openable door of a dirt collection region being in an open configuration, and with the suction source drawing air out of the cyclone bin assembly via the auxiliary cyclone air outlet.

For example, as exemplified in FIG. 32, a valve 640c is provided to selectively direct suction from a main suction source 220 to either cyclone air outlet 634 (for drawing air through cyclone 31 during normal operation of the surface cleaning apparatus) or to bypass inlet 636 (for drawing air from dirt collection region 38 via cyclone 31 during emptying). Valve 640c may be a sliding panel which selectively blocks the outlet of main pre-motor filter 202 and alternate pre-motor filter 650. Accordingly, a single closure member may be used.

Accordingly, during a cleaning operation, valve 640c may direct an airflow generated by main suction fan 204 to induce an airflow from dirty air inlet 602 through cyclone air inlet 632, around cyclone 31, through cyclone air outlet 634, through pre-motor filter 202, past the suction motor, across post-motor filter 208, and exiting from clean air outlet 604 of the surface cleaning apparatus.

During emptying of the dirt collection region, valve 640c (in the position shown in FIG. 32) may direct an airflow generated by suction fan 204 to induce an airflow from the dirt collection region 38 via cyclone dirt outlet 633 and cyclone 31, and through an auxiliary cleaning cyclone air outlet through cleaning cycle pre-motor filter 650, past the suction motor and through post-motor filter 208 to clean air outlet 604. This may result in some or all of any particles dispersed in a plume or cloud following the opening of dirt collection region 38 being drawn back into auxiliary pre-motor filter 650. As the dirt that may be entrained by a pre-motor filter may differ between a cleaning operation and an emptying operation, (e.g., it may be finer during a cleaning operation) each pre-motor filter 202 and 650 may be designed to collect dirt having a different particle size distribution. An advantage of this design is that the main pre-motor filter 202 is not used in an emptying mode and therefore the pre-motor filter may operate for a longer period of time without requiring cleaning or replacement.

In an alternate embodiment, a separate closure member may be used for each flow path. Accordingly, for example, in the embodiment of FIG. 31, a main closure member 640c may be used to close the cyclone air outlet during an emptying mode and an alternate closure member 640d may be used to close the alternate downstream air flow path 612 during a cleaning mode.

As noted above, it will be appreciated that in some embodiments, suction motor 206 may be operated at reduced power during an emptying operation so that only very fine dust or other particles may be drawn towards auxiliary pre-motor filter 650, while larger particles may be relatively unaffected by the reduced airflow.

As used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

While the above description describes features of example embodiments, it will be appreciated that some features and/or functions of the described embodiments are susceptible to modification without departing from the spirit and principles of operation of the described embodiments. For example, the various characteristics which are described by means of the represented embodiments or examples may be selectively combined with each other. Accordingly, what has been described above is intended to be illustrative of the claimed concept and non-limiting. It will be understood by persons skilled in the art that other variants and modifications may be made without departing from the scope of the invention as defined in the claims appended hereto. The scope of the claims should not be limited by the preferred embodiments and examples, but should be given the broadest interpretation consistent with the description as a whole.

The invention claimed is:

1. An apparatus comprising one or more of a surface treatment apparatus having an air treatment member and a refuse container wherein at least one of the surface treatment apparatus and the refuse container comprises:
    a dust control member providing a dust control agent comprising one or more of a liquid mist, positive ions and negative ions, wherein the dust control member directs the dust control agent to an area that is located below a dirt emptying outlet of a dirt collection region of the surface treatment apparatus when the dirt collection region of the surface treatment apparatus oriented such that dirt exits the dirt collection region in a downward direction.

2. The apparatus as claimed in claim 1 wherein the one of the surface treatment apparatus and the refuse container comprises both the dust control member and a treatment applicator that provides a treatment agent comprising one or more of a deodorizing agent, a disinfecting agent and a sanitizing agent to an interior volume of the refuse container.

3. The apparatus as claimed in claim 2 wherein the treatment agent comprises one or more of ozone, UV light and hydrogen peroxide.

4. The apparatus as claimed in claim 3 wherein the apparatus further comprises a hood which, when the dirt emptying outlet is open and the hood is in a deployed position, a closed volume is provided that includes the interior volume of the refuse container and an interior volume of the dirt collection region and the treatment agent is introduced into the closed volume.

5. The apparatus as claimed in claim 2 wherein the treatment agent comprises ozone and the refuse container further comprises an air flow path extending from the interior volume of the refuse container to a clean air outlet, the air flow path including a suction motor and an ozone destructor material.

6. The apparatus as claimed in claim 2 wherein the treatment agent is provided at pre-set intervals.

7. The apparatus as claimed in claim 2 wherein the treatment agent is provided by manual activation.

8. The apparatus as claimed in claim 2 wherein the treatment agent is provided subsequent to emptying of the dirt collection region.

9. The apparatus as claimed in claim 1 wherein the dust control member comprises one or more nozzles directed to the area below the dirt emptying outlet of the dirt collection region of the surface treatment apparatus when the dirt collection region of the surface treatment apparatus is oriented such that dirt exits the dirt collection region in a downward direction.

10. The apparatus as claimed in claim 9 wherein the one or more nozzles introduce the dust control agent to a location below the dirt emptying outlet and above the bottom of the refuse container.

11. The apparatus as claimed in claim 10 wherein the apparatus further comprises a hood which, when the dirt emptying outlet is open and the hood is in a deployed position, a closed volume is provided that includes the interior volume of the refuse container and an interior volume of the dirt collection region and the one or more nozzles introduce the dust control agent into the closed volume.

12. The apparatus as claimed in claim 9 wherein the surface cleaning apparatus comprises a dirt separation member having the dirt emptying outlet and the one or more nozzles are located around at least part of the perimeter of the dirt separation member.

13. The apparatus as claimed in claim 9 wherein the one or more nozzles are provided on the refuse container.

14. The apparatus as claimed in claim 1 wherein the dust control member is automatically actuated when the dirt emptying outlet is opened.

15. The apparatus as claimed in claim 1 wherein the dust control member is automatically actuated prior to the dirt emptying outlet being opened.

16. The apparatus as claimed in claim 1 wherein the one of the surface treatment apparatus and the refuse container which has the dust control member further comprises a dust control agent reservoir.

17. The apparatus as claimed in claim 1 wherein the refuse container further comprises a suction motor having a suction motor inlet end in air flow communication with the interior volume of the refuse container and a suction motor outlet end in air flow communication with the ambient atmosphere exterior to the refuse container.

18. The apparatus of claim 17 further comprising an air flow path extending from the interior volume to a clean air outlet, the air flow path including the suction motor and a refuse container air treatment member.

19. The apparatus of claim 18 wherein the refuse container air treatment member comprises a cyclone.

20. The apparatus of claim 19 further comprising a pre-motor filter positioned in the air flow path upstream of the suction motor.

21. The apparatus as claimed in claim 1 wherein the treatment agent is provided after a pre-set number of uses of the surface cleaning apparatus.

* * * * *